(12) United States Patent
Robinson et al.

(10) Patent No.: US 11,318,243 B2
(45) Date of Patent: May 3, 2022

(54) SYSTEM AND METHODS FOR THE TREATMENT OF WOUNDS WITH DRESSING HAVING CLOSED CELLS

(71) Applicant: KCI Licensing, Inc., San Antonio, TX (US)

(72) Inventors: Timothy Mark Robinson, Shillingstone (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 840 days.

(21) Appl. No.: 16/060,326

(22) PCT Filed: Dec. 13, 2016

(86) PCT No.: PCT/US2016/066392
§ 371 (c)(1),
(2) Date: Jun. 7, 2018

(87) PCT Pub. No.: WO2017/119996
PCT Pub. Date: Jul. 13, 2017

(65) Prior Publication Data
US 2020/0139025 A1 May 7, 2020

Related U.S. Application Data

(60) Provisional application No. 62/275,595, filed on Jan. 6, 2016.

(51) Int. Cl.
*A61F 13/02* (2006.01)
*A61M 1/00* (2006.01)

(52) U.S. Cl.
CPC .......... *A61M 1/85* (2021.05); *A61F 13/0216* (2013.01); *A61M 1/74* (2021.05); *A61M 1/90* (2021.05);
(Continued)

(58) Field of Classification Search
CPC .......... A61F 13/00068; A61F 13/0216; A61M 1/0031; A61M 1/0058; A61M 1/0084;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Kai H Weng

(57) ABSTRACT

In one example embodiment, a system for treating a tissue site is disclosed that may comprise a manifold including a non-porous film having a plurality of closed cells defined by a sealed region perforated with apertures extending through the sealed region, wherein the manifold is adapted to contact the tissue site. The system may further comprise a cover adapted to provide a fluid seal between a therapeutic environment including the manifold proximate one side of the cover and a local external environment on the other side of the cover. In one embodiment, the plurality of closed cells is adapted to form distal channels with the cover and the apertures are adapted to provide fluid communication between the distal channels and the tissue site. The system may further comprise a negative-pressure source fluidly
(Continued)

coupled to the therapeutic environment and adapted to provide negative pressure through the distal channels and the apertures to the tissue site. In another example embodiment, a method for treating a tissue site is disclosed comprising positioning a manifold including a non-porous film having a plurality of closed cells defined by a sealed region perforated with apertures extending through the seals to contact the tissue site. The method may further comprise covering the manifold and the tissue site with a drape to provide a fluid seal between a therapeutic environment including the manifold proximate one side of the drape and a local external environment the other side of the drape. The method may further comprise providing negative pressure from a negative-pressure source coupled to the therapeutic environment wherein the negative pressure is applied through the distal channels and the apertures to the tissue site.

49 Claims, 12 Drawing Sheets

(52) U.S. Cl.
CPC . *A61M 2205/3344* (2013.01); *A61M 2205/50* (2013.01)

(58) Field of Classification Search
CPC ........ A61M 1/0088; A61M 2205/3344; A61M 2205/50
See application file for complete search history.

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,220,476 B2 | 5/2007 | Sperry et al. |
| 7,721,781 B2 | 5/2010 | Sperry et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,777,911 B2 | 7/2014 | Heagle et al. |
| 8,834,451 B2 | 9/2014 | Blott et al. |
| 8,870,837 B2 | 10/2014 | Locke et al. |
| 8,926,592 B2 | 1/2015 | Blott et al. |
| 9,017,302 B2 | 4/2015 | Vitaris et al. |
| 9,198,801 B2 | 12/2015 | Weston |

(56) References Cited

U.S. PATENT DOCUMENTS

| | | | |
|---|---|---|---|
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2005/0228329 | A1 | 10/2005 | Boehringer et al. |
| 2007/0239078 | A1* | 10/2007 | Jaeb ............... A61F 13/00068 601/2 |
| 2008/0275409 | A1* | 11/2008 | Kane ............... A61F 13/00068 604/305 |
| 2010/0106115 | A1* | 4/2010 | Hardman ............ A61M 27/00 604/319 |
| 2010/0160877 | A1* | 6/2010 | Kagan ............... A61M 1/90 604/319 |
| 2011/0034906 | A1* | 2/2011 | Malhi ............... A61M 27/00 604/543 |
| 2011/0213287 | A1* | 9/2011 | Lattimore ......... A61F 13/00021 602/46 |
| 2013/0072850 | A1* | 3/2013 | Locke ............... A61L 15/42 604/20 |
| 2014/0163491 | A1 | 6/2014 | Schuessler et al. |
| 2015/0080788 | A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2815731 A1 | 12/2014 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 08/036162 A2 | 3/2008 |
| WO | 2009021523 A1 | 2/2009 |
| WO | 2014140578 A1 | 9/2014 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, YU. A., et al; "Vacuum Therapy in the Treatment of Purulent Lactation Mastitis"; Vestnik Khirurgi, May 14, 1986, pp. 66-70, and 9 page English translation thereof.

Yusupov. YU.N., et al; "Active Wound Drainage", Vestnki Khirurgi, vol. 138, Issue 4, 1987, and 7 page English translation thereof.

Davydov, YU.A., et al; "Bacteriological and Cytological Assessment of Vacuum Therapy for Purulent Wounds"; Vestnik Khirugi, Oct. 1988, pp. 48-52, and 8 page English translation thereof.

Davydov, YU.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous or Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

(56) References Cited

OTHER PUBLICATIONS

F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report for corresponding International Application No. PCT/U2016/066392 dated Apr. 26, 2017.
Written Opinion for corresponding International Application No. PCT/US2016/066392 dated Apr. 26, 2017.
Chinese First Office Action for Corresponding Application No. 2016800824899, dated Jul. 1, 2020.
Extended European Search Report for Corresponding Application No. 20163307.0, dated Jun. 8, 2020.

* cited by examiner

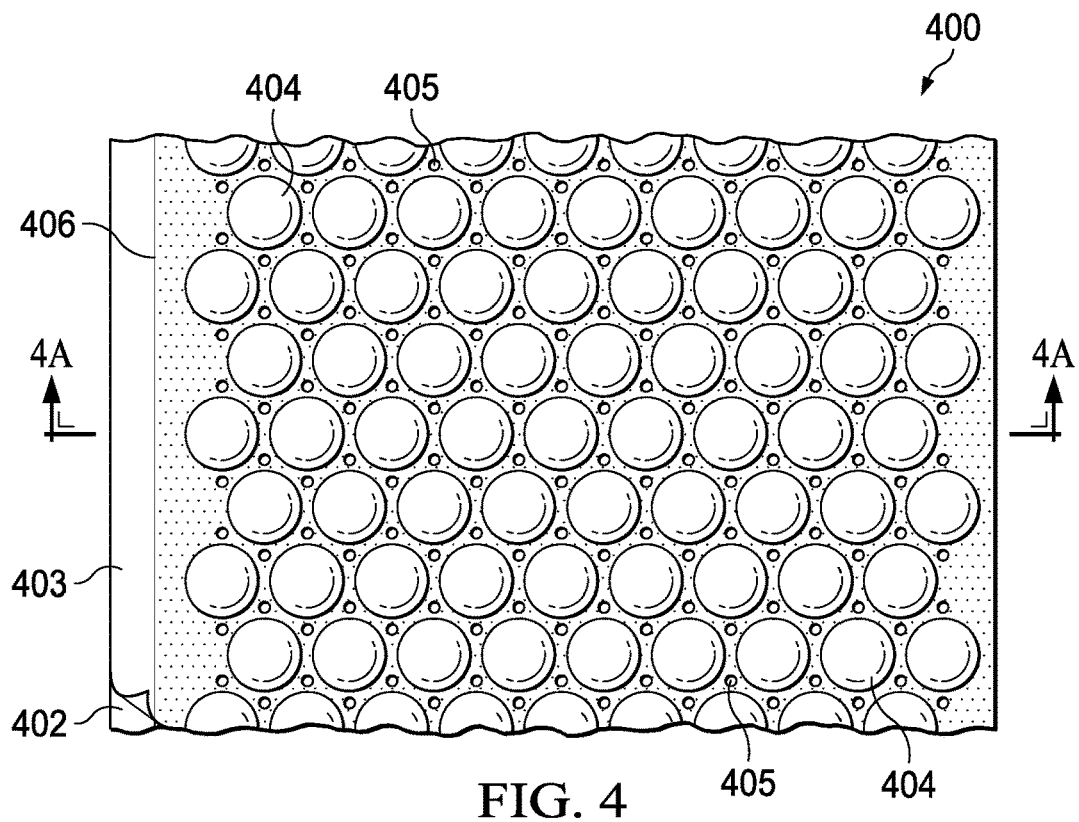
FIG. 4
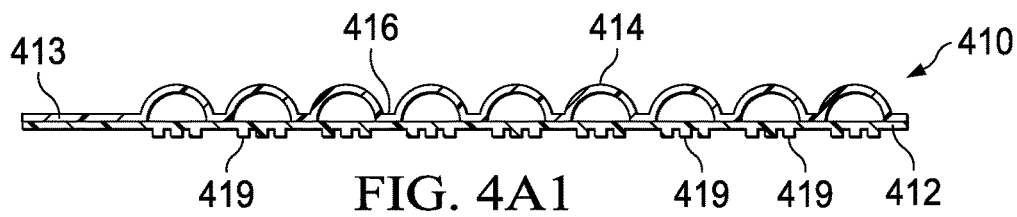
FIG. 4A1
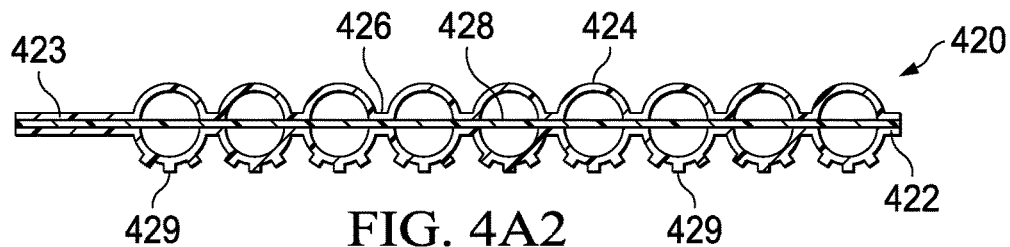
FIG. 4A2
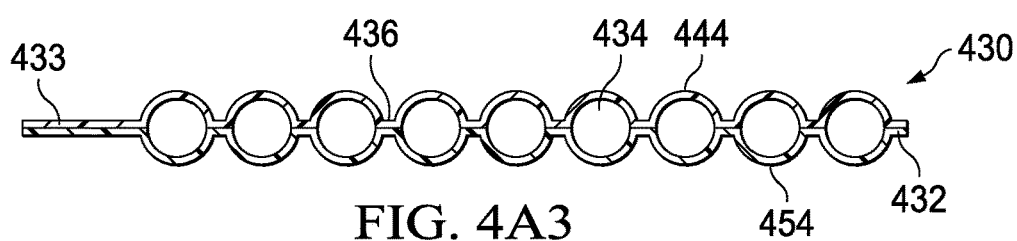
FIG. 4A3

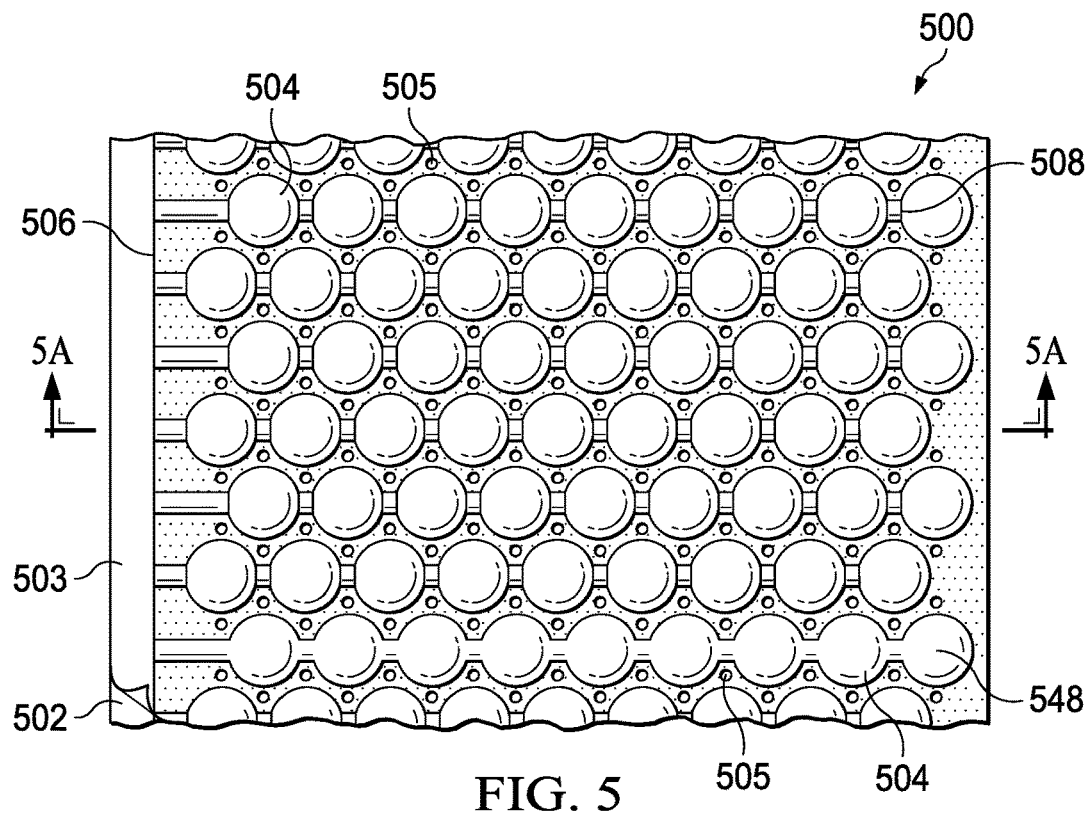
FIG. 5
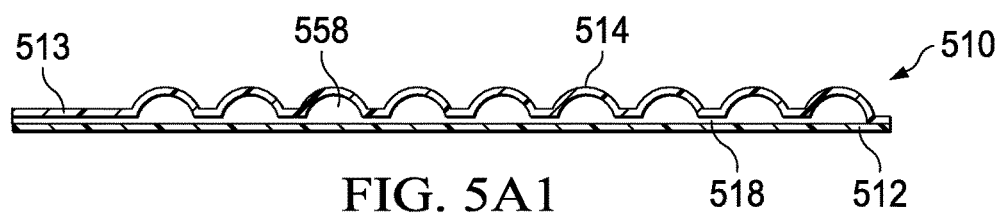
FIG. 5A1
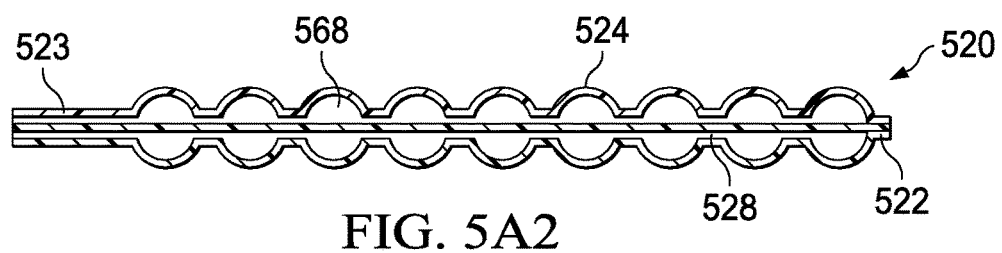
FIG. 5A2
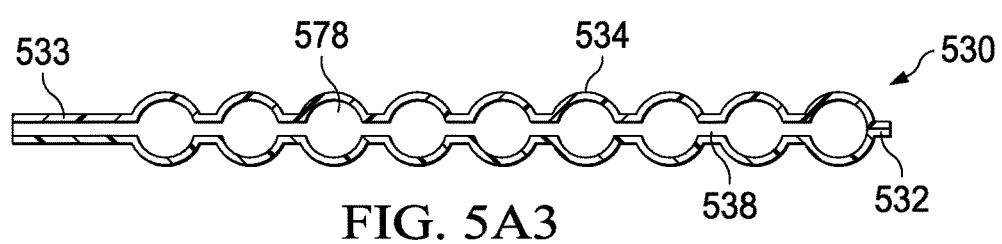
FIG. 5A3

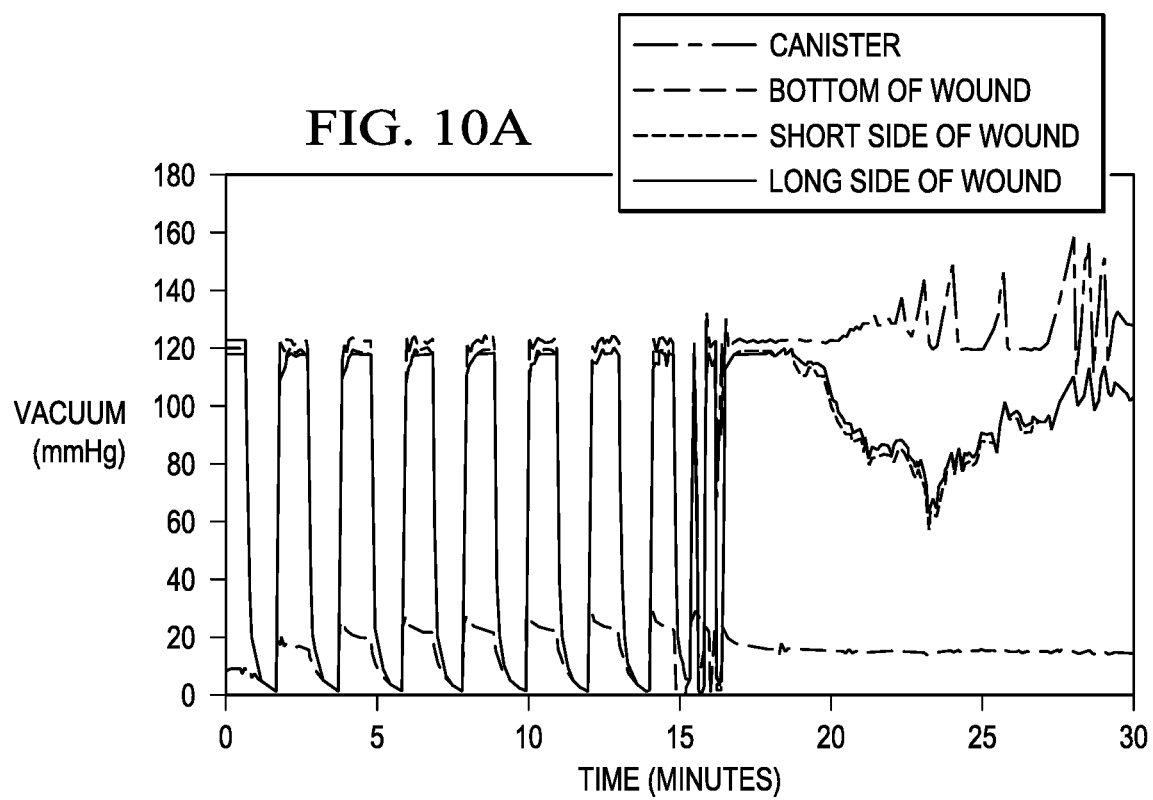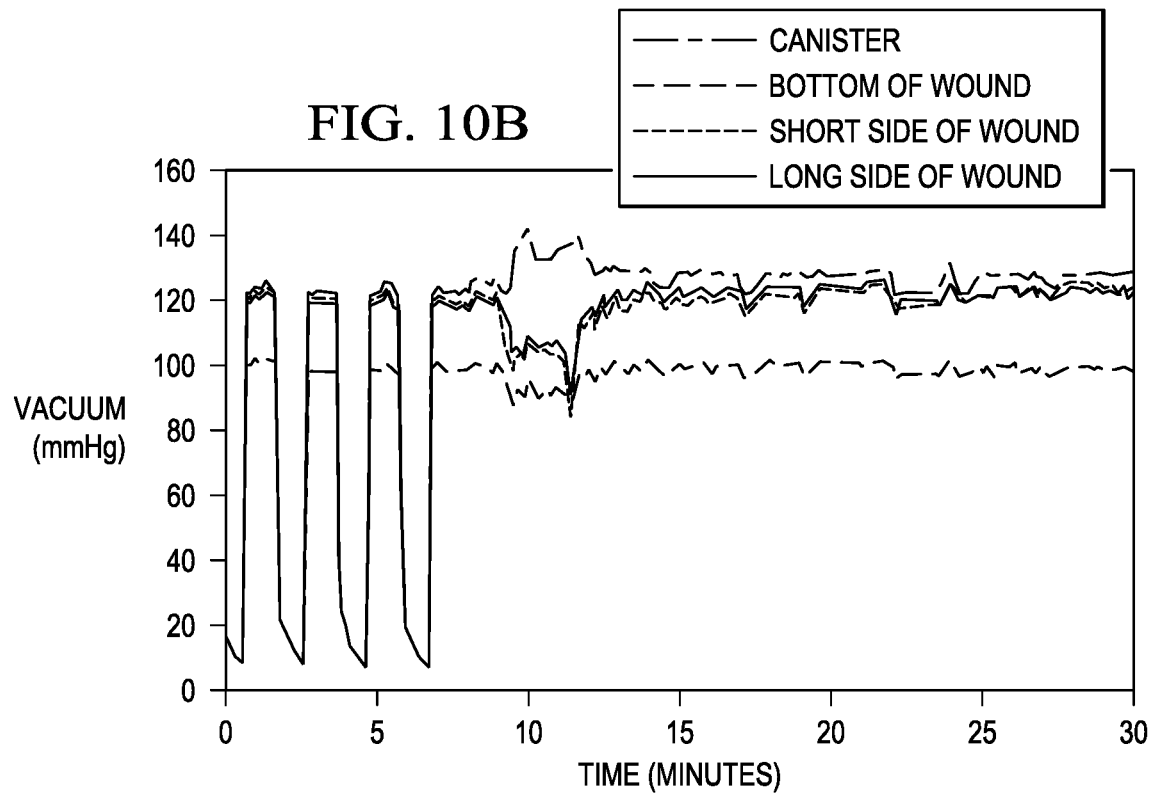

SYSTEM AND METHODS FOR THE TREATMENT OF WOUNDS WITH DRESSING HAVING CLOSED CELLS

RELATED APPLICATION

This application claims the benefit, under 35 USC 119(e), of the filing of U.S. Provisional Patent Application No. 62/275,595, entitled "Systems and Methods for the Treatment of Wounds with Dressing Having Closed Cells," filed 6 Jan. 2016, which is incorporated herein by reference for all purposes.

TECHNICAL FIELD

The invention set forth in the appended claims relates generally to tissue treatment systems and more particularly, but without limitation, to treating wounds with negative pressure and instillation utilizing a dressing having closed cells and perforations in a negative-pressure and instillation therapy environment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

"Instillation" is another practice that generally refers to a process of slowly introducing fluid to a tissue site and leaving the fluid for a prescribed period of time before removing the fluid. For example, a wound can be washed out with a stream of liquid solution, or a cavity can be washed out using a liquid solution for therapeutic purposes. Moreover, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

Wound dressings may include a foam or fibrous manifold covered by a drape that forms a seal over the tissue site so that the manifold can distribute negative pressure and instill fluids to the tissue site. The structure of such manifolds may also generate macro and micro strains at the tissue site to enhance granulation. Such manifolds often must be left at the tissue site for several days or more and consequently must be removed when they become clogged with tissue ingrowth and exudates from the tissue site. Before such manifolds are replaced, every piece of such manifolds must be completely removed so that the tissue site does not become contaminated with infection. Once the manifold is removed, a fresh manifold is disposed at the tissue site to continue therapy.

BRIEF SUMMARY

New and useful systems, apparatuses, and methods for treating wounds that utilize dressings having closed cells and perforations or apertures in a negative-pressure and instillation therapy environment are set forth in the appended claims. Illustrative embodiments are also provided to enable a person skilled in the art to make and use the claimed subject matter.

For example, in some embodiments, instillation and negative pressure therapy systems and methods are especially effective for improving tissue granulation when used in conjunction with a sheet of closed cells formed from polymeric sheets and joined by a sealed region including perforations or apertures extending through the seals. A number of different textures and shapes also may be formed on the sheets of closed cells that would face the tissue site to further improve granulation when used with instillation and negative pressure therapy. Such a polymeric structure significantly reduces tissue ingrowth and does not shed fibers or particulates when shaped for positioning at a tissue site or removed from a tissue site.

More specifically, in one example embodiment, a system for treating a tissue site may comprise a manifold including a non-porous film having a plurality of closed cells defined by a sealed region perforated with apertures extending through the seals, wherein the manifold is adapted to contact the tissue site. The system may further comprise a cover adapted to provide a fluid seal between a therapeutic environment including the manifold proximate one side of the cover and a local external environment on the other side of the cover. In one embodiment, the plurality of closed cells is adapted to form distal channels with the cover and the apertures are adapted to provide fluid communication between the distal channels and the tissue site. The system may further comprise a negative-pressure source fluidly coupled to the therapeutic environment and adapted to provide negative pressure through the distal channels and the apertures to the tissue site.

Alternatively, in another example embodiment, a method for treating a tissue site is disclosed comprising positioning a manifold including a non-porous film having a plurality of closed cells defined by a sealed region perforated with apertures extending through the seals to contact the tissue site. The method may further comprise covering the manifold and the tissue site with a drape to provide a fluid seal between a therapeutic environment including the manifold proximate one side of the drape and a local external environment the other side of the drape. The method may further comprise forming distal channels between the plurality of closed cells and the drape wherein the apertures are adapted to provide fluid communication between the distal channels and the tissue site. The method may further comprise providing negative pressure from a negative-pressure source coupled to the therapeutic environment wherein the negative pressure is applied through the distal channels and the apertures to the tissue site.

Alternatively, in another example embodiment, a dressing for treating a tissue site is disclosed comprising a manifold including a non-porous film having a plurality of closed cells defined by a sealed region perforated with apertures extending through the seals, wherein the manifold is adapted to contact the tissue site. The dressing may further comprise a cover adapted to provide a fluid seal between a therapeutic environment including the manifold proximate one side of the cover and a local external environment on the other side of the cover. As such, the plurality of closed cells may be adapted to form distal channels with the cover and the apertures are adapted to provide fluid communication between the distal channels and the tissue site. The therapeutic environment is adapted to receive negative pressure that is applied through the distal channels and the apertures to the tissue site.

In another example embodiment, a dressing may include a non-porous manifold covered by a drape that forms a seal over the tissue site so that the manifold can distribute negative pressure and instill fluids to the tissue site. The structure of such manifolds may also generate macro and micro strains at the tissue site to enhance granulation. Such manifolds may be left at the tissue site for several days or more and often must be removed when they become clogged with tissue ingrowth and exudates from the tissue site. It is desirable to reduce the amount of tissue ingrowth that may cause pain or discomfort when the manifold is removed from the tissue site after the negative pressure and instillation therapies have been applied for several days or more. It is also desirable to reduce the amount of remnants from a manifold structure that may be left at the tissue site when removed, particularly for tissue sites that granulate quickly, for manifold structures left at the tissue site for three days or more, and/or for manifold material that tends to shed or release particles into the tissue site. It is also desirable to use a manifold structure that is able to generate macro and micro strains at a tissue site to enhance granulation without significant tissue ingrowth or shedding remnants of material when removed.

In another example embodiment, a manifold for treating a tissue site may be used in a dressing wherein the manifold comprises a first sheet of non-porous polymeric film and a second sheet of non-porous polymeric film sealed to the first sheet of non-porous polymeric film forming a sealed region between the first sheet and the second sheet. The manifold further comprises a plurality of closed cells formed in at least one of the first sheet and the second sheet, wherein the closed cells each have a base defined by the sealed region. The manifold also comprises a plurality of apertures perforating the sealed region to provide fluid flow through the first sheet and the second sheet. The manifold is adapted to be positioned and sealed at the tissue site by a cover that forms distal channels with the closed cells and the sealed space for receiving and distributing fluids to the tissue site through the apertures. The manifold is a single component comprising a plurality of closed cells separated by a sealed region, and apertures extending through the sealed region such that the manifold provides both a manifold function and a filler function when positioned between the tissue site and the cover.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 4 is a plan view of a first embodiment of a sheet of closed cells formed from a web of nonporous, polymeric film that may be used as a manifold in the negative-pressure and instillation therapy system of FIGS. 1 and 1A;

FIG. 4A1 is a cross-sectional view taken along line 4A-4A in FIG. 4 of a first embodiment of closed cells;

FIG. 4A2 is a cross-sectional view taken along line 4A-4A in FIG. 4 of a second embodiment of closed cells;

FIG. 4A3 is a cross-sectional view taken along line 4A-4A in FIG. 4 of a third embodiment of closed cells;

FIG. 5 is a plan view of a second embodiment of a sheet of closed cells formed from a web of nonporous, polymeric film that may be used as a manifold in the negative-pressure and instillation therapy system of FIGS. 1 and 1A;

FIG. 5A1 is a cross-sectional view taken along line 5A-5A in FIG. 5 of a first embodiment of closed cells;

FIG. 5A2 is a cross-sectional view taken along line 5A-5A in FIG. 5 of a second embodiment of closed cells;

FIG. 5A3 is a cross-sectional view taken along line 5A-5A in FIG. 5 of a third embodiment of closed cells;

FIGS. 10A and 10B are both are charts that illustrate the negative pressure variations (mmHg) over time (minutes) provided to the manifold of FIG. 9 as compared to pressure measurements at the (i) bottom of the tissue site, (ii) the short side edge of the tissue site, and (iii) the long side edge of the tissue site;

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the technology.

Figure 1:
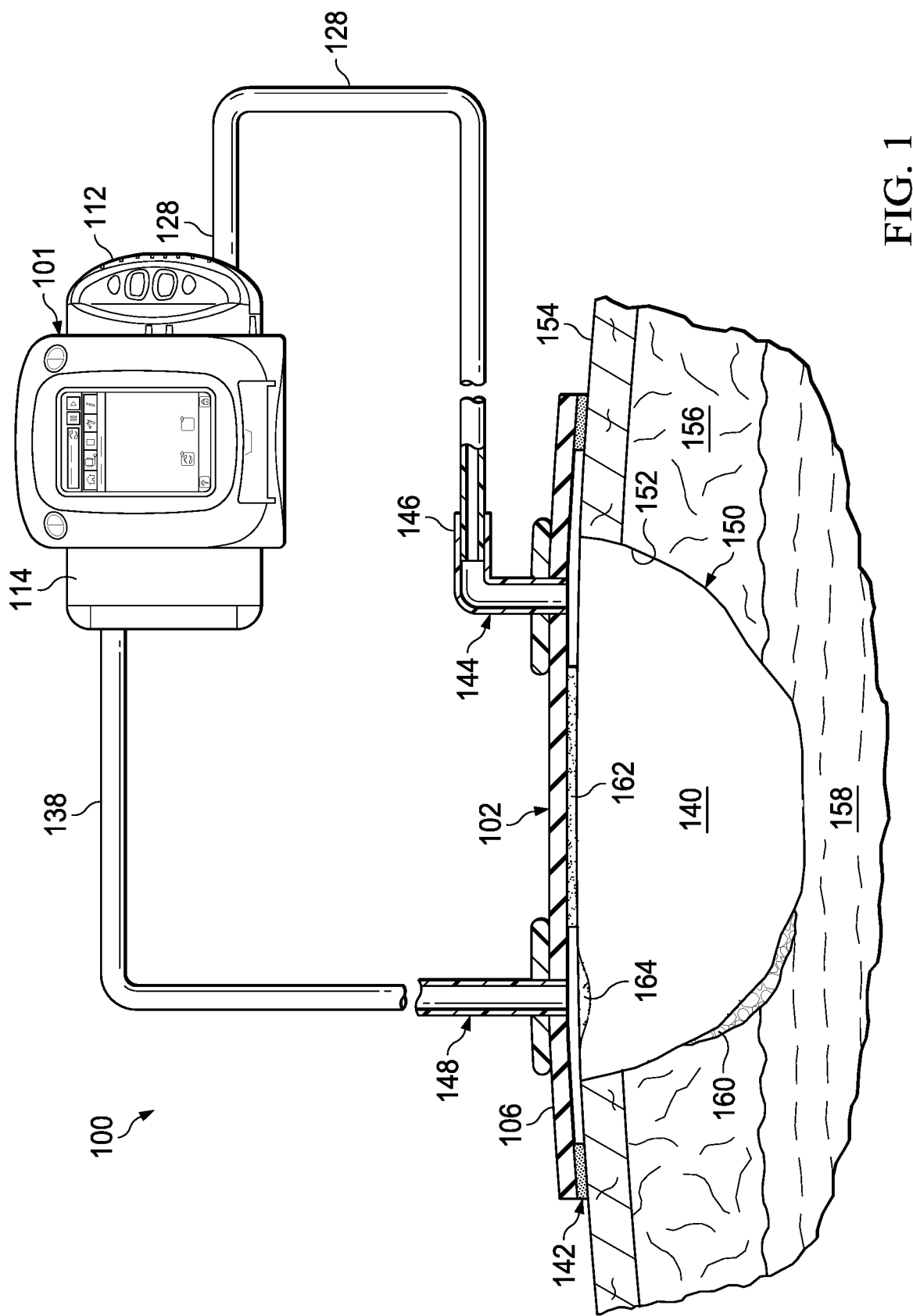
FIG. 1 is a schematic cross-section of an example embodiment of a negative-pressure and instillation therapy system for delivering treatment solutions to a dressing comprising a manifold disposed at a tissue site for delivering negative pressure and treatment solutions to the tissue site.
Figure 1A:
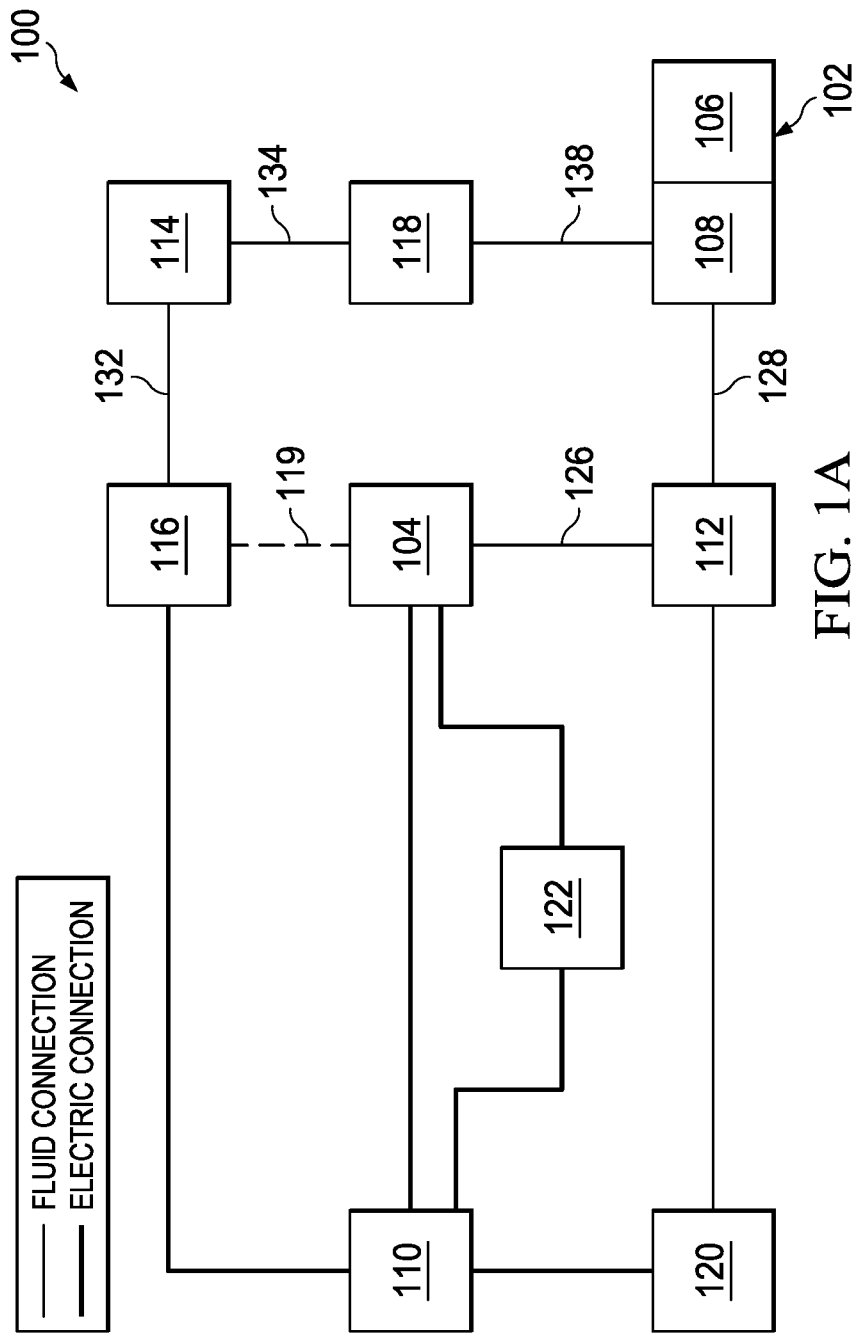
FIG. 1A is a functional block diagram of an example embodiment of a therapy system of FIG. 1 that can deliver treatment solutions in accordance with this specification.

The present technology also provides negative pressure therapy devices and systems, and methods of treatment using such systems with antimicrobial solutions. FIG. 1 is a schematic diagram of an example embodiment of a negative-pressure and instillation therapy system for delivering treatment solutions to a dressing at a tissue site. FIG. 1A is a simplified functional block diagram of an example embodiment of a therapy system 100 that can provide negative-pressure therapy with instillation of treatment solutions in accordance with this specification. The therapy system 100 may be packaged as a single, integrated unit such as therapy system 101. The therapy system 101 may be, for example, a V.A.C. Ulta™ System available from Kinetic Concepts, Inc. of San Antonio, Tex.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1A. A dressing may include a cover, a tissue interface, or both in some embodiments. The dressing 102, for example, may include a cover 106 and a tissue interface 108. A regulator or a controller, such as a controller 110, may also be coupled to the negative-pressure source 104. The therapy system 100 may optionally include a fluid container, such as a container 112, coupled to the dressing 102 and to the negative-pressure source 104.

The therapy system 100 may also include a source of instillation solution. For example, a solution source 114 may be fluidly coupled to the dressing 102, as illustrated in the example embodiment of FIG. 1. The solution source 114 may be fluidly coupled to a positive-pressure source such as the positive-pressure source 116 in some embodiments, or may be fluidly coupled to the negative-pressure source 104. A regulator, such as an instillation regulator 118, may also be fluidly coupled to the solution source 114 and the dressing 102. In some embodiments, the instillation regulator 118 may also be fluidly coupled to the negative-pressure source 104 through the dressing 102, as illustrated in the example of FIG. 1. In some embodiments, the negative-pressure source 104 and the positive-pressure source 116 may be a single pressure source or unit as indicated by dashed line 119.

Additionally, the therapy system 100 may include sensors to measure operating parameters and provide feedback signals to the controller 110 indicative of the operating parameters. As illustrated in FIG. 1, for example, the therapy system 100 may include a pressure sensor 120, an electric sensor 122, or both, coupled to the controller 110. The pressure sensor 120 may also be coupled or configured to be coupled to a distribution component and to the negative-pressure source 104.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the tissue interface 108 of the dressing 102 through the container 112 by conduits 126 and 128. Additionally, the positive-pressure source 116 may be directly coupled to the controller 110, and may be indirectly coupled to the tissue interface 108 through the solution source 114 and the instillation regulator 118 by conduits 132, 134 and 138.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit, such as therapy system 101. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold 140. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site. In some illustrative embodiments, the pathways of a manifold may be interconnected to improve distribution or collection of fluids across a tissue site. In some embodiments, a manifold may additionally or alternatively comprise projections that form interconnected fluid pathways. For example, a manifold may be molded to provide surface projections that define interconnected fluid pathways.

The tissue interface 108 may be either hydrophobic or hydrophilic. Examples of hydrophilic materials include polyvinyl alcohol and polyether. The tissue interface 108 may exhibit hydrophilic characteristics and include hydrophobic foams that have been treated or coated to provide hydrophilic characteristics. The tissue interface 108 may further promote granulation at a tissue site when pressure within the sealed therapeutic environment is reduced. For example, any or all of the surfaces of the tissue interface 108 may have an uneven, coarse, or jagged profile that can induce micro-strains and stresses at a tissue site when negative pressure is applied through the tissue interface 108 such as, for example, protrusions or other regular or irregular shapes.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m$^2$ per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device, such as an attachment device 142, may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In some embodiments, a dressing interface may facilitate coupling the negative-pressure source 104 to the dressing 102. The negative pressure provided by the negative-pressure source 104 may be delivered through the conduit 128 to a negative-pressure interface 144, which may include an elbow port 146. In one illustrative embodiment, the negative-pressure interface 144 is a T.R.A.C.® Pad or Sensa T.R.A.C.® Pad available from KCI of San Antonio, Tex. The negative-pressure interface 144 allows the negative pressure to be delivered to the cover 106 and realized within an interior portion of the cover 106 and the manifold 140. In this illustrative, non-limiting embodiment, the elbow port 146 extends through the cover 106 to the manifold 140, but numerous arrangements are possible.

Therapy system 100 may also include a second interface that may facilitate coupling of the positive-pressure source 116 to the dressing 102, such as fluid-delivery interface 148. The positive pressure provided by the positive-pressure source 116 may be delivered through the conduit 138. The fluid-delivery interface 148 also may be fluidly coupled to the dressing 102 and may pass through a hole cut in the cover 106. The hole cut in the cover 106 for the fluid-delivery interface 148 may be separated from its location or other hole cut in the cover 106 through which the negative-pressure interface 144 may pass. The fluid-delivery interface 148 may allow for a fluid, such as an antimicrobial solution of the present technology, to be delivered by the therapy system 100 through the cover 106 and to the manifold 140. In some embodiments, the fluid-delivery interface 148 may include an inlet pad. The inlet pad may be a material that is not sound-absorbing. In some embodiments, the inlet pad may be an elastomer. For example, the inlet pad may be an elastic polymer, such as polyurethane, thermoplastic elastomers, polyether block amide (PEBAX), polyisoprene, polychloroprene, chlorosulphonated polythene, and polyisobutylene, blends and copolymers. In one illustrative embodiment, the fluid-delivery interface 148 and the negative-pressure interface 144 may be integrated into a single pad for the delivery and removal of solutions from the tissue site 150, such as a V.A.C. Vera T.R.A.C.™ Pad available from Kinetic Concepts, Inc. of San Antonio, Tex.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 120 or the electric sensor 122, are generally known in the art as any apparatus operable to detect or measure a physical phenomenon or property, and generally provide a signal indicative of the phenomenon or property that is detected or measured. For example, the pressure sensor 120 and the electric sensor 122 may be configured to measure one or more operating parameters of the therapy system 100. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The electric sensor 122 may optionally measure operating parameters of the negative-pressure source 104, such as the voltage or current, in some embodiments. Preferably, the signals from the pressure sensor 120 and the electric sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The solution source 114 may also be representative of a container, canister, pouch, bag, or other storage component, which can provide a solution for instillation therapy. The solutions for instillation therapy may comprise antimicrobial solutions that vary according to a prescribed therapy. In other embodiments, methods may further comprise administration of other therapeutic solutions. Examples of such other therapeutic solutions that may be suitable for some prescriptions include hypochlorite-based solutions, silver nitrate (0.5%), sulfur-based solutions, biguanides, cationic solutions, and isotonic solutions. In one illustrative embodiment, the solution source 114 may include a storage component for the solution and a separate cassette for holding the storage component and delivering the solution to the tissue site 150, such as a V.A.C. VeraLink™ Cassette available from Kinetic Concepts, Inc. of San Antonio, Tex.

In operation, the tissue interface 108 may be placed within, over, on, or otherwise proximate to a tissue site, such as tissue site 150. The cover 106 may be placed over the tissue interface 108 and sealed to an attachment surface near the tissue site 150. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

As discussed above, the tissue site 150 may include, without limitation, any irregularity with a tissue, such as an open wound, surgical incision, or diseased tissue. The therapy system 100 is presented in the context of a tissue site that includes a wound 152, which is through the epidermis 154, or generally skin, and the dermis 156 and reaching into a hypodermis, or subcutaneous tissue 158. The therapy system 100 may be used to treat a wound of any depth, as well as many different types of wounds including open wounds, incisions, or other tissue sites. The tissue site 150 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 150 may include removal of fluids originating from the tissue site 150, such as exudates or ascites, or fluids instilled into the dressing to cleanse or treat the tissue site 150, such as antimicrobial solutions. The wound 152 may include undesirable tissue 160, biofilm 162 formed on any living or nonliving surface of the dressing 102 or the tissue site 150, and planktonic microbes 164 floating or swimming in liquid medium in and around the dressing 102. The therapy system 100 may be used in broader contexts, including with any type of tissue site including wounds, defects, or other treatment target located on or within living or nonliving tissue.

In one embodiment, controller 110 receives and processes data, such as data related to the pressure distributed to the tissue interface 108 from the pressure sensor 120. The controller 110 may also control the operation of one or more components of therapy system 100 to manage the pressure distributed to the tissue interface 108 for application to the wound 152 at the tissue site 150, which may also be referred to as the wound pressure (WP). In one embodiment, controller 170 may include an input for receiving a desired target pressure (TP) set by a clinician or other user and may be program for processing data relating to the setting and inputting of the target pressure (TP) to be applied to the tissue site 150. In one example embodiment, the target pressure (TP) may be a fixed pressure value determined by a user/caregiver as the reduced pressure target desired for therapy at the tissue site 150 and then provided as input to the controller 110. The user may be a nurse or a doctor or other approved clinician who prescribes the desired negative pressure to which the tissue site 150 should be applied. The desired negative pressure may vary from tissue site to tissue site based on the type of tissue forming the tissue site 150, the type of injury or wound 152 (if any), the medical condition of the patient, and the preference of the attending physician. After selecting the desired target pressure (TP), the negative-pressure source 104 is controlled to achieve the target pressure (TP) desired for application to the tissue site 150.

Figure 2A:
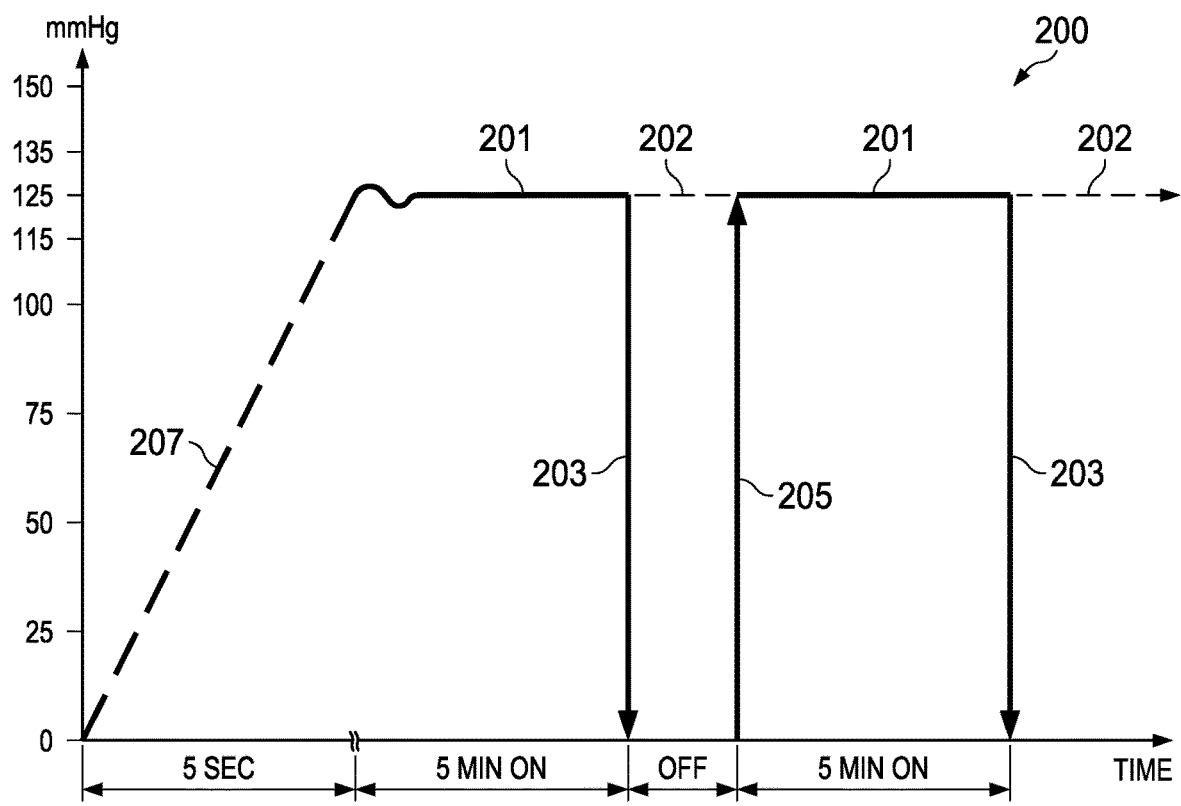
FIG. 2A is a graph illustrating an illustrative embodiment of pressure control modes for the negative-pressure and instillation therapy system of FIGS. 1 and 1A wherein the x-axis represents time in minutes (min) and/or seconds (sec) and the y-axis represents pressure generated by a pump in Torr (mmHg) that varies with time in a continuous pressure mode and an intermittent pressure mode that may be used for applying negative pressure in the therapy system.

Referring more specifically to FIG. 2A, a graph illustrating an illustrative embodiment of pressure control modes 200 that may be used for the negative-pressure and instillation therapy system of FIGS. 1 and 1A is shown wherein the x-axis represents time in minutes (min) and/or seconds (sec) and the y-axis represents pressure generated by a pump in Torr (mmHg) that varies with time in a continuous pressure mode and an intermittent pressure mode that may be used for applying negative pressure in the therapy system. The target pressure (TP) may be set by the user in a continuous pressure mode as indicated by solid line 201 and dotted line 202 wherein the wound pressure (WP) is applied to the tissue site 150 until the user deactivates the negative-pressure source 104. The target pressure (TP) may also be set by the user in an intermittent pressure mode as indicated by solid lines 201, 203 and 205 wherein the wound pressure (WP) is cycled between the target pressure (TP) and atmospheric pressure. For example, the target pressure (TP) may be set by the user at a value of 125 mmHg for a specified period of time (e.g., 5 min) followed by the therapy being turned off for a specified period of time (e.g., 2 min) as indicated by the gap between the solid lines 203 and 205 by venting the tissue site 150 to the atmosphere, and then repeating the cycle by turning the therapy back on as indicated by solid line 205 which consequently forms a square wave pattern between the target pressure (TP) level and atmospheric pressure.

In some example embodiments, the decrease in the wound pressure (WP) at the tissue site 150 from ambient pressure to the target pressure (TP) is not instantaneous, but rather gradual depending on the type of therapy equipment and dressing being used for the particular therapy treatment. For example, the negative-pressure source 104 and the dressing 102 may have an initial rise time as indicated by the dashed line 207 that may vary depending on the type of dressing and therapy equipment being used. For example, the initial rise time for one therapy system may be in the range between about 20-30 mmHg/second or, more specifically, equal to about 25 mmHg/second, and in the range between about 5-10 mmHg/second for another therapy system. When the therapy system 100 is operating in the intermittent mode, the repeating rise time as indicated by the solid line 205 may be a value substantially equal to the initial rise time as indicated by the dashed line 207.

The target pressure may also be a variable target pressure (VTP) controlled or determined by controller 110 that varies in a dynamic pressure mode. For example, the variable target pressure (VTP) may vary between a maximum and minimum pressure value that may be set as an input determined by a user as the range of negative pressures desired for therapy at the tissue site 150. The variable target pressure (VTP) may also be processed and controlled by controller 110 that varies the target pressure (TP) according to a predetermined waveform such as, for example, a sine waveform or a saw-tooth waveform or a triangular waveform, that may be set as an input by a user as the predetermined or time-varying reduced pressures desired for therapy at the tissue site 150.

Figure 2B:
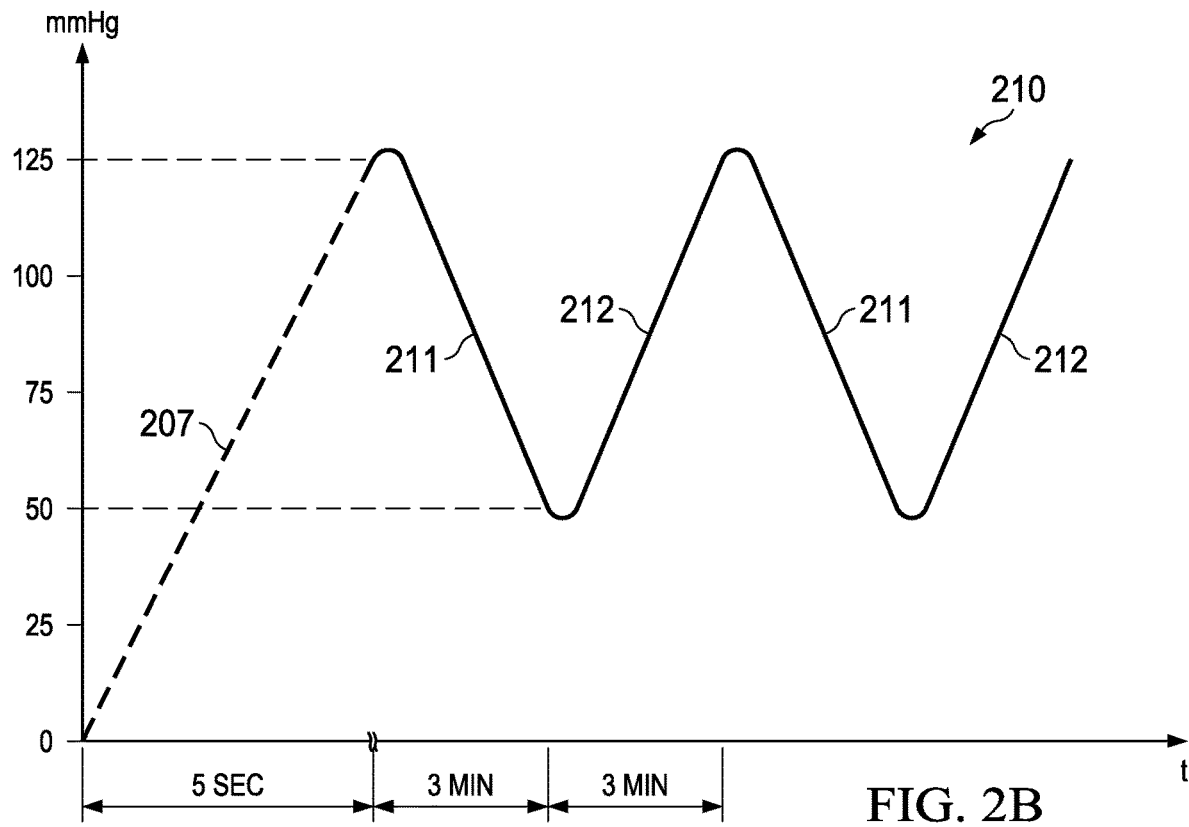
FIG. 2B is a graph illustrating an illustrative embodiment of another pressure control mode for the negative-pressure and instillation therapy system of FIGS. 1 and 1A wherein the x-axis represents time in minutes (min) and/or seconds (sec) and the y-axis represents pressure generated by a pump in Torr (mmHg) that varies with time in a dynamic pressure mode that may be used for applying negative pressure in the therapy system.

Referring more specifically to FIG. 2B, a graph illustrating an illustrative embodiment of another pressure control mode for the negative-pressure and instillation therapy system of FIGS. 1 and 1A is shown wherein the x-axis represents time in minutes (min) and/or seconds (sec) and the y-axis represents pressure generated by a pump in Torr (mmHg) that varies with time in a dynamic pressure mode that may be used for applying negative pressure in the therapy system. For example, the variable target pressure (VTP) may be a reduced pressure that provides an effective treatment by applying reduced pressure to tissue site 150 in the form of a triangular waveform varying between a minimum and maximum pressure of 50-125 mmHg with a rise time 212 set at a rate of +25 mmHg/min and a descent time 211 set at −25 mmHg/min, respectively. In another embodiment of the therapy system 100, the variable target pressure (VTP) may be a reduced pressure that applies reduced pressure to tissue site 150 in the form of a triangular waveform varying between 25-125 mmHg with a rise time 212 set at a rate of +30 mmHg/min and a descent time 211 set at −30 mmHg/min. Again, the type of system and tissue site determines the type of reduced pressure therapy to be used.

Figure 3:
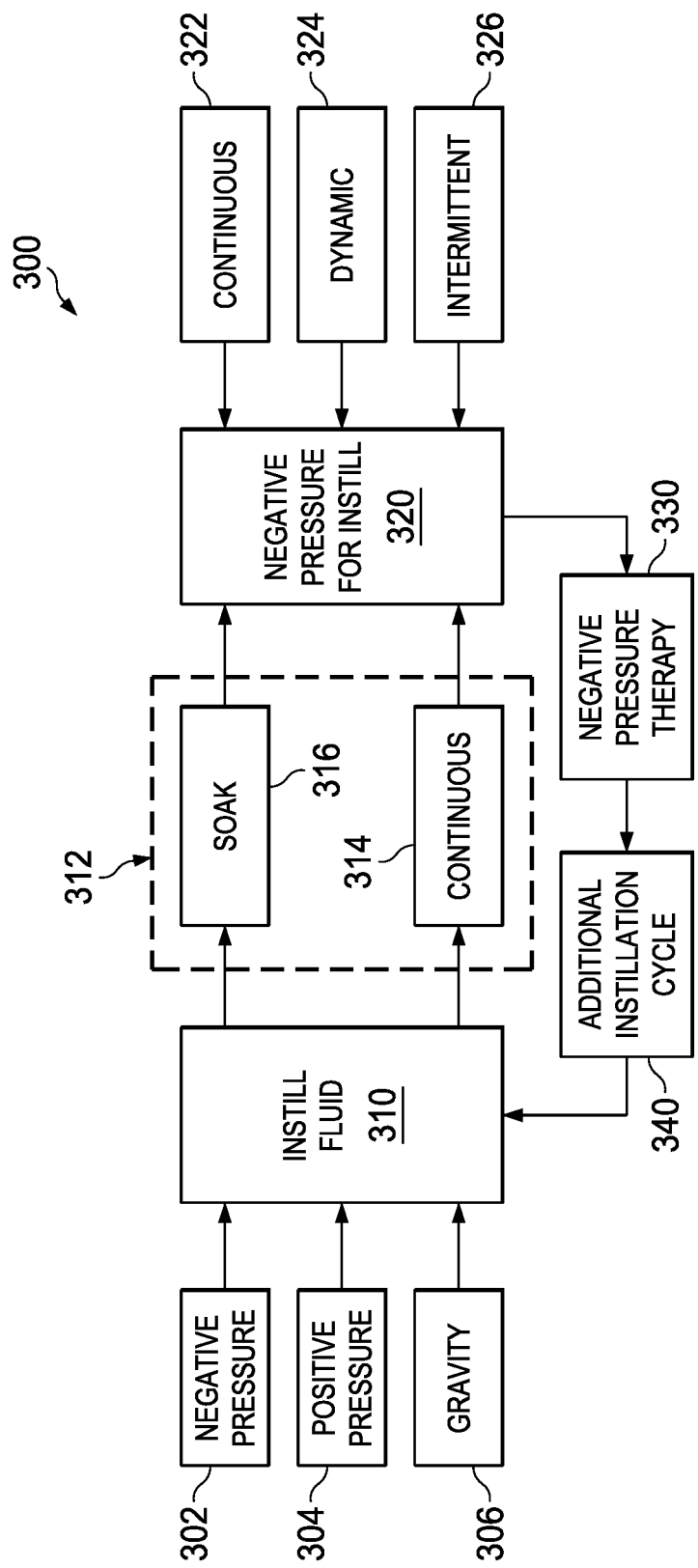
FIG. 3 is a flow chart showing an illustrative embodiment of a therapy method for providing negative-pressure and instillation therapy for delivering treatment solutions to a dressing at a tissue site.

FIG. 3 is a flow chart illustrating an illustrative embodiment of a therapy method 300 that may be used for providing negative-pressure and instillation therapy for delivering an antimicrobial solution or other treatment solution to a dressing at a tissue site. In one embodiment, the controller 110 receives and processes data, such as data related to fluids provided to the tissue interface. Such data may include the type of instillation solution prescribed by a clinician, the volume of fluid or solution to be instilled to the tissue site ("fill volume"), and the amount of time needed to soak the tissue interface ("soak time") before applying a negative pressure to the tissue site. The fill volume may be, for example, between 10 and 500 mL, and the soak time may be between one second to 30 minutes. The controller 110 may also control the operation of one or more components of the therapy system 100 to manage the fluids distributed from the solution source 114 for instillation to the tissue site 150 for application to the wound 152 as described in more detail above. In one embodiment, fluid may be instilled to the tissue site 150 by applying a negative pressure from the negative-pressure source 104 to reduce the pressure at the tissue site 150 to draw the instillation fluid into the dressing 102 as indicated at 302. In another embodiment, fluid may be instilled to the tissue site 150 by applying a positive pressure from the negative-pressure source 104 (not shown) or the positive-pressure source 116 to force the instillation fluid from the solution source 114 to the tissue interface 108 as indicated at 304. In yet another embodiment, fluid may be instilled to the tissue site 150 by elevating the solution source 114 to height sufficient to force the instillation fluid into the tissue interface 108 by the force of gravity as indicated at 306. Thus, the therapy method 300 includes instilling fluid into the tissue interface 108 by either drawing or forcing the fluid into the tissue interface 108 as indicated at 310.

The therapy method 300 may control the fluid dynamics of applying the fluid solution to the tissue interface 108 at 312 by providing a continuous flow of fluid at 314 or an intermittent flow of fluid for soaking the tissue interface 108 at 316. The therapy method 300 may include the application of negative pressure to the tissue interface 108 to provide either the continuous flow or intermittent soaking flow of fluid at 320. The application of negative pressure may be implemented to provide a continuous pressure mode of operation at 322 as described above to achieve a continuous flow rate of instillation fluid through the tissue interface 108 or a dynamic pressure mode of operation at 324 as described above to vary the flow rate of instillation fluid through the tissue interface 108. Alternatively, the application of negative pressure may be implemented to provide an intermittent mode of operation at 326 as described above to allow instillation fluid to soak into the tissue interface 108 as described above. In the intermittent mode, a specific fill volume and the soak time may be provided depending, for example, on the type of wound 152 being treated and the type of dressing 102 being utilized to treat the wound 152. After or during instillation of fluid into the tissue interface 108 has been completed, the therapy method 300 may begin may be utilized using any one of the three modes of operation at 330 as described above. The controller 110 may be utilized to select any one of these three modes of operation and the duration of the negative pressure therapy as described above before commencing another instillation cycle at 340 by instilling more fluid at 310.

In some illustrative embodiments, the manifold 140 may comprise two sheets of non-porous, polymeric film having inner surfaces coupled together to form sealed regions defining a plurality of closed cells. When the manifold 140 is positioned at the tissue site and negative pressure is applied as described above, the closed cells formed by the non-porous, polymeric film do not completely collapse from apposition forces resulting from the application of negative pressure or instillation fluid to the manifold 140 and the tissue site. The two sheets of non-porous, polymeric film may be a single sheet of material having two laminae or two separate sheets that are coupled together to form the closed cells. The sheets of non-porous, polymeric film may initially be separate sheets that are brought into superposition and sealed or they may be formed by folding a single sheet unto itself with a heat sealable surface facing inward. Each sheet of the non-porous, polymeric film also may be a monolayer or multilayer structure depending on the application or the desired structure of the closed cells.

The sheets of non-porous, polymeric film may comprise any flexible material that can be manipulated to enclose closed cells, including various thermoplastic materials, e.g., polyethylene homopolymer or copolymer, polypropylene homopolymer or copolymer, etc. Non-limiting examples of suitable thermoplastic polymers include polyethylene homopolymers, such as low density polyethylene (LDPE) and high density polyethylene (HDPE), and polyethylene copolymers such as, e.g., ionomers, EVA, EMA, heterogeneous (Zeigler-Natta catalyzed) ethylene/alpha-olefin copolymers, and homogeneous (metallocene, single-cite catalyzed) ethylene/alpha-olefin copolymers. Ethylene/alpha-olefin copolymers are copolymers of ethylene with one or more comonomers selected from $C_3$ to $C_{20}$ alpha-olefins, such as 1-butene, 1-pentene, 1-hexene, 1-octene, methyl pentene and the like, in which the polymer molecules comprise long chains with relatively few side chain branches, including linear low density polyethylene (LLDPE), linear medium density polyethylene (LMDPE), very low density polyethylene (VLDPE), and ultra-low density polyethylene (ULDPE). Various other materials are also suitable such as, e.g., polypropylene homopolymer or polypropylene copolymer (e.g., propylene/ethylene copolymer), polyesters, polystyrenes, polyamides, polycarbonates, etc.

As indicated above, it is desirable that the closed cells formed by the non-porous, polymeric film are resistant to collapsing from the negative pressure or instillation fluid when either one is applied to the manifold 140 and the tissue site. In one embodiment, the polymeric film possesses sufficient tensile strength to resist stretching under the apposition forces created by negative pressure wound therapy. The tensile strength of a material is the ability of material to resist stretching as represented by a stress-strain curve where stress is the force per unit area, i.e., pascals (Pa), newtons per square meter ($N/m^2$), or pounds per square inch (psi). The ultimate tensile strength (UTS) is the maximum stress the material can withstand while being stretched before failing or breaking Many materials display a linear elastic behavior defined by a linear stress-strain relationship often extending up to a nonlinear region represented by the yield point, i.e., the yield strength of a material. For example, high density polyethylene (HDPE) has a high tensile strength and low-density polyethylene (LDPE) has a slightly lower tensile strength, which are suitable materials for the sheets of non-porous, polymeric film as set forth above. Linear low density polyethylene (LLDPE) is often used as well because the material stretches very little as the force is increased up to the yield point of the material. Thus, the closed cells are able to resist collapsing (or stretching) when subjected to an external force or pressure. For example, the yield strength of HDPE ranges from 26-33 MPa which has a UTS of 37 MPa, while LDPE has somewhat lower values. Therefore, in some example embodiments, it is desirable that the non-porous, polymeric film has a yield strength greater than about 20 MPa. For example, rubber has a yield strength and a UTS of only 16 MPa and consequently is extremely stretchable and susceptible to breaking with the application on little pressure.

Referring more specifically to FIGS. 4 and 4A1-4A3, one example embodiment of the manifold 140 is a manifold 400 that comprises two sheets of non-porous, polymeric film, sheet 402 and sheet 403, having inner surfaces coupled to each other to form a sealed region 406 defining a plurality of closed cells 404. The inner surfaces may be coupled to each other to form closed cells 404 that are substantially airtight to inhibit excessive collapsing of the closed cells from the application of negative pressure which could block the flow of fluid through the manifold. In one example embodiment, the sealed region 406 may be formed by a heat seal between the inner surfaces of the sheets 402 and 403. In another example embodiment, the sealed region 406 may be formed by adhesion between the sheets 402 and 403. Alternatively, sheets 402 and 403 may be adhesively bonded to each other. The closed cells 404 may be substantially airtight when formed and have an internal pressure that is substantially an ambient pressure. In another example embodiment, the closed cells 404 may be inflated with air or other suitable gases such as, for example, carbon dioxide or nitrogen. The closed cells 404 may be inflated to have an internal pressure greater than the atmospheric pressure to maintain their shape and resistance to collapsing under pressure. For example, the closed cells 404 may be inflated to a pressure up to about 25 psi above the atmospheric pressure so that they do not collapse as described above.

The sealed region 406 comprises sealed segments between the closed cells 404 that may be flexible enough so that the manifold 400 is sufficiently flexible to conform to the shape the tissue site. The sealed segments may be sufficiently flexible or sized so that the manifold 400 may be folded into two or more layers that are positioned at the tissue site to provide optimal negative pressure and instillation therapy to the tissue site as described in more detail below. The sealed segments of the sealed region 406 serve as common boundaries between adjacent closed cells 404. The sealed segments of the sealed region 406 may also be perforated to provide pathways for fluids to flow through the manifold 400. In one example embodiment, the sealed region 406 may include a plurality of apertures 405 that are formed between the closed cells 404 in the sealed region 406 and extend through both of the sheets 402 and 403 to permit fluids to flow through the manifold 400. The number of apertures may vary depending on the type of negative pressure and instillation therapy to provide an by the system as described in more detail above. The apertures may have different shapes such as, for example, circular, elliptical, or rectangular, or other irregular shape. Such apertures may have a diameter, major axis, or length between about 0.5 mm and 1.5 mm. In another example embodiment, the apertures may be formed by a slit cut through segments of the sealed region 406.

The sealed region 406 may define the base or the cross-sectional shape of the closed cells 404 as being generally circular as shown, but in other embodiments may define the base as being a rectangular or triangular shape, hexagonal, or other geometric or an irregular shape. The closed cells 404 may be formed with a volumetric shape corresponding to the cross-sectional shape of the closed cells 404. For example, the volumetric shape may be generally hemispherical or spherical in shape as shown. In other example embodiments, the closed cells 404 may be formed with a volumetric shape that is generally conical, cylindrical, tubular having a flattened or hemispherical end, or geodesic shape. The closed cells 404 that are generally hemispherical or spherical in shape may have a diameter between about 0.5 mm and 10 mm. The closed cells 404 also may have a pitch, i.e., the center to center distance between each of the closed cells 404, between about 1.5 mm and 15 mm. Because the sealed region 406 defines the base of the closed cells 404 including the diameter of a circular base and the pitch of adjacent closed cells 404, the surface area of the manifold 400 covered by the closed cells 404 may also be determined as a percentage, i.e., the cell coverage percentage. In one example embodiment wherein the diameter of the closed cells 404 is about 1.0 mm and the pitch is about 2.0 mm, the cell coverage percentage is about 22% of the surface area of the manifold 400. In another example embodiment wherein the diameter of the closed cells 404 is about 2.0 mm and the pitch is about 5.0 mm, the cell coverage percentage is about 14% of the surface area of the manifold 400. In yet another example embodiment wherein the diameter of the closed cells 404 is about 1.0 mm and the pitch is about 1.5 mm, the cell coverage percentage is about 30% of the surface area of the manifold 400. In still another example embodiment wherein the diameter of the closed cells 404 is about 1.5 mm, the pitch is about 2.0 mm, and the closed cells 404 are more tightly arranged such that there are about 28.5 cells in a 10 $mm^2$ section of the manifold 400, the cell coverage percentage is about 51% of the surface area of the manifold 400. Depending on the diameter, pitch, and arrangement of the closed cells 404, the cell coverage percentage may range between about 10% and about 55% of the surface area of a manifold. Closed cells 404 having other base shapes or volumetric shapes also may have a cell coverage percentage in generally the same range.

As indicated above, embodiments of the closed cells 404 may have volumetric shapes including hemispherical shapes, spherical shapes, conical shapes, cylindrical shapes, or tubular shapes formed with a flattened or hemispherical end. These volumetric shapes may be formed in one or both sheets 402 and 403 such as the single hemispherical shape shown in FIG. 4A1 (closed cells 414) and the two hemispherical shapes that are aligned with one another to form a spherical shape as shown in FIG. 4A3 (closed cells 434). The closed cells 404 may have a height between about 0.25 mm and about 5 mm, e.g., about half the diameter of closed cells 404 having a hemispherical shape as described in the examples above. In another example embodiment, the closed cells 404 may have a generally tubular shape formed with generally parallel walls extending from the sealed region 406 to a hemispherical end. In yet another example embodiment, closed cells 404 having a tubular shape may have a diameter of about 1.5 mm and an average height in a range between about 2.0 mm and 4.0 mm. It should be understood that any reference to the closed cells may apply equally to any of the volumetric shapes described above.

The sheets 402 and 403 may each have a thickness of about 5 µm to 500 µm, and the sealed region 406 may have a thickness between about 10 µm and 1000 µm. The walls of the closed cells 404 after being formed by coupling the sheets 402 and 403 together may have a thickness relative to the thickness of the sheets 402 and 403 defined by a draw ratio which is the ratio of the average height of the closed cells 404 to the average thickness of the sheets 402 and 403. In one example embodiment where the closed cells 404 have a generally tubular shape, the sheets 402 and 403 may have an average thickness of 250 μm and the closed cells 404 may have an average height in a range between about 2.0 mm and 4.0 mm with a diameter of about 1.5 mm Consequently, the closed cells 404 have a draw ratio ranging from about 8:1 to about 16:1 for heights of 2.0 and 4.0 mm, respectively. In another example embodiment, the sheets 402 and 403 may have an average thickness of 100 μm and the closed cells 404 may have an average height in a range between about 2.0 mm and 4.0 mm with a diameter of about 1.5 mm Consequently, the closed cells 404 have a draw ratio ranging from about 20:1 to about 40:1 for heights of 2.0 and 4.0 mm, respectively. In yet other example embodiments, it is desirable that the draw ratio be greater than about 16:1 where the thickness of the sheets 402 and 403 is less than about 250 μm. The sheets 402 and 403 may each have the same or different thicknesses and flexibilities, but are substantially non-stretchable as described above so that the closed cells 404 maintain a generally constant volume without bursting after negative pressure or instillation fluid are applied to the manifold 400. Consequently, even when a load is applied to the manifold 400 which squeezes closed cells 404 into a different shape, the closed cells 404 are sufficiently flexible to recover their original shape after being squeezed without bursting.

In one example embodiment, the closed cells 404 may be formed in only one of the sheets 402 and 403 so that they extend from only one side of the sealed region 406 such as, for example, closed cells 414 having a hemispherical shape as shown in FIG. 4A1. More specifically, the manifold 400 may be a manifold 410 that comprises two sheets of polymeric film, sheet 412 and sheet 413, having inner surfaces coupled to each other in a pattern defining a plurality of closed cells 414. The sheets 412 and 413 may be sealed to each other in a sealed region 416 that defines the closed cells 414 that are generally hemispherical in shape. The closed cells 414 may be formed on only one side of the sealed region 416 by using sheets of polymeric film having a different thickness or flexibility. For example, the closed cells 414 may be formed in the sheet 413 by applying a vacuum to the sheet 413 where the sheet 412 is sufficiently thicker than the sheet 413 to withstand the vacuum being applied and retain a generally planar shape. One skilled in the art understands that closed cells 414 having other shapes may be formed to extend from only one side of the sealed region 406 and that such cells may be formed by using a variety of different methods. For example, the closed cells 414 may be formed separately in the sheet 413 which is subsequently coupled to the sheet 412 that may have the same thickness as the sheet 413 so that the sealed region 416 remains thin and flexible.

In another example embodiment, the closed cells 404 may be formed in both of the sheets 402 and 403 so that they extend from both sides of the sealed region 406 such as, for example, hemispherical closed cells shown in FIG. 4A3. More specifically, the manifold 400 may be a manifold 430 that comprises two sheets of polymeric film, sheet 432 and sheet 433, having inner surfaces coupled to each other in a pattern defining a plurality of closed cells in both sheet 432 and sheet 433. For example, the closed cells formed in each of the sheets 432 and 433 may be hemispherical in shape such as, for example, hemispherical cell 444 and hemispherical cell 454, that are aligned to form a single closed cell 434 having a generally spherical shape as shown in FIG. 4A3. In other words, each of the single closed cells 434 comprises two hemispherical cells, hemispherical cell 444 and hemispherical cell 454, formed in the sheets 432 and 433, respectively. The sheets 432 and 433 may be sealed to each other in a sealed region 436 that defines the closed cells 434 that are generally spherical in shape. In other example embodiments, the closed cells in each sheet may not be aligned with each other, but rather overlap or aligned with the sealed portion of the opposite sheet. (Not shown.) The closed cells 434 may be formed on both sides of the sealed region 436 by using sheets of polymeric film having a different thickness or flexibility. For example, the shape of the closed cells 434 may be asymmetric when the sheets 432 and 433. However, when the sheets 432 and 433 have substantially identical thickness or flexibility, the shape of the closed cells 434 may be substantially spherical as shown in FIG. 4A3.

In yet another embodiment, the manifold 400 may comprise a third sheet (not shown) forming a multi-sheet configuration wherein the third sheet is disposed between the sheets 402 and 403 to form closed cells 404 that may be generally spherical in shape formed by two hemispherical sections separated by portions of the third sheet of material. Referring more specifically to FIG. 4A2, the manifold 400 may be a manifold 420 that comprises sheet 422 and sheet 423 of polymeric film having inner surfaces coupled or bonded to a third sheet 428 to form sealed region 426 defining a plurality of closed cells 424. The closed cells 424 are generally spherical in shape and formed by two hemispherical sections that are separated by portions of the third sheet 428. Sheet 422 and sheet 423 may be coupled or bonded to the third sheet 428 using a variety of different methods including, for example, melting (e.g., RF, ultrasonic, and heat), adhesives using both hot melt and solvents, and pressing techniques. The manifold 420 may also be formed by combining two of the manifolds 410 together by coupling or bonding the outside planar surface of the sheet 412 of each manifold 410 together to form the manifold 420. The third sheet 428 may be formed from a polymeric film and may also be perforated to permit airflow between the two hemispherical sections of the closed cells 424. When the third sheet 428 is formed from a polymeric material, the third sheet 428 may also be textured to provide wicking capability. The third sheet 428 may also be formed from a polyester material to provide wicking within the closed cells 424, and may further include fibers flocked into the polyester material to provide additional wicking capability. The third sheet 428 also may include an antimicrobial layer or antimicrobials coated on the third sheet 428.

Figure 4B:
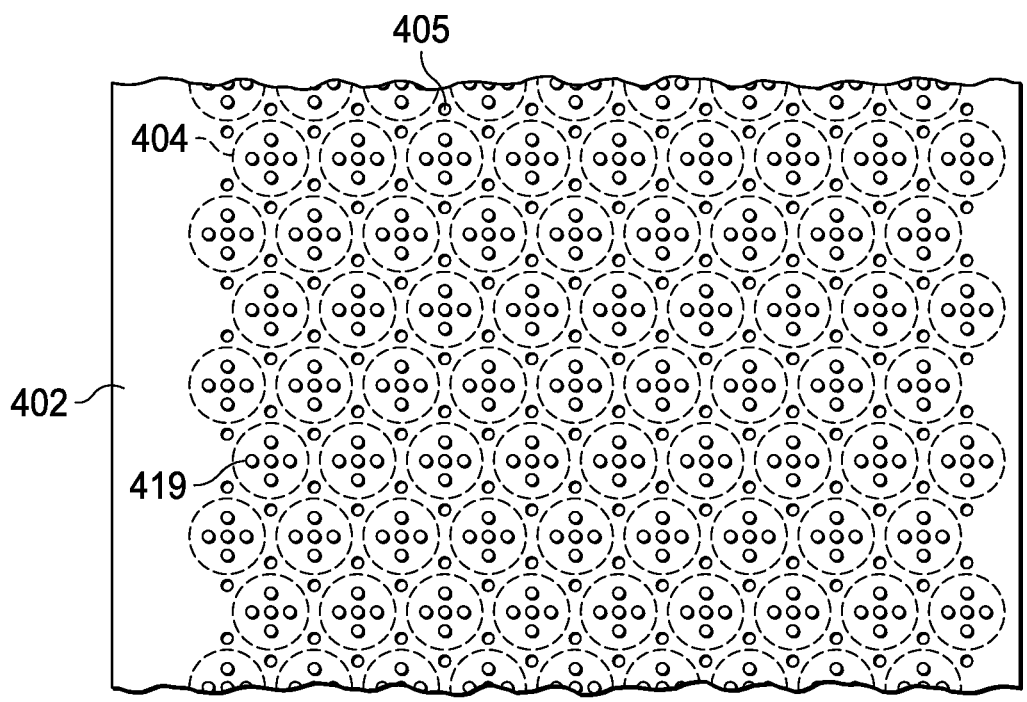
FIG. 4B is a rear view of the sheet of closed cells shown in FIG. 4 including nodes projecting from the sheet.
Figure 4C:
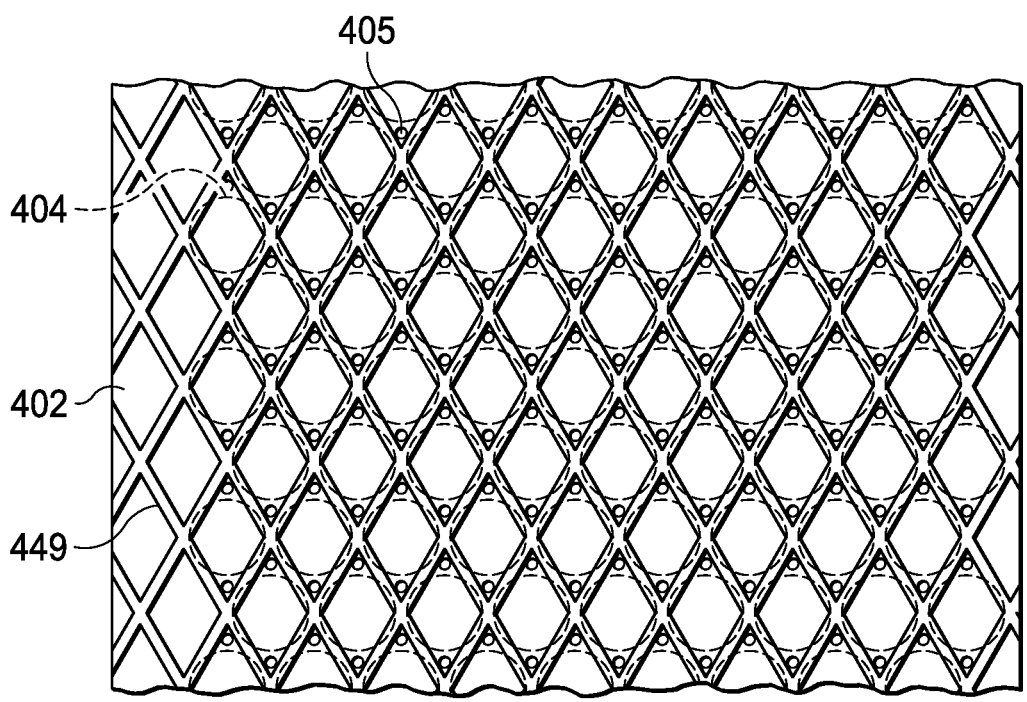
FIG. 4C is a rear view of the sheet of closed cells shown in FIG. 4 including a textured pattern projecting from the sheet.

When the manifolds 400, 410, 420 and 430 are disposed at the tissue site, each one may have one of its polymeric film sheets facing the tissue site and, more specifically, an outer surface of the tissue-facing sheet. The outer surface of the tissue-facing sheet may be textured with surface features, which may be protrusions or indentations, to enhance fluid flow through the manifolds and to increase micro-strains against the tissue site to enhance granulation. More specifically, the outer side of the sheet facing the tissue site may further comprise a pattern of individual nodes or projections embossed on the outer surface of the sheet, a grid embossed on the outer surface of the sheet, a pattern or grid of grooves formed into the outer surface of the sheet, or any combination of the foregoing. In one exemplary embodiment as shown in FIGS. 4A1 and 4B, projections or nodes 419 may be embossed on the outer surface of the sheet 412 that is generally planar so that the nodes 419 contact the tissue site when the manifold 410 is positioned at the tissue site. In another exemplary embodiment as shown in FIG. 4A2, projections or nodes 429 may be embossed on the outer surface of the sheet 422 and, more specifically, on the surface of the closed cells 424 so that the nodes 429 contact the tissue site when the manifold 420 is positioned at the tissue site. A number of different textures or shapes may be formed on the outside surface of the sheet 402 that is flat and would face the tissue site when in use. In one exemplary embodiment, a grid 449 may be embossed or extruded in a woven pattern on the outer surface of the tissue-facing sheet, e.g., sheet 402 or sheet 412, as shown in FIG. 4C. The pattern of the grid 449 may have a variety of shapes like the diamond-shaped pattern shown. It should be understood that many types of protrusions or grids may be formed on the tissue-facing surface of a sheet of any one of the manifolds 400, 410, 420 and 430 to enhance fluid flow through the manifolds and/or enhance granulation of the tissue site. Moreover, it should be understood that any of such protrusions or grids may be formed by embossing, welding, or any other similar type of coupling mechanism.

As indicated above, the nodes 419 may be projections that are flexible or rigid. In one embodiment, the projections may be formed from a substantially gas impermeable material such as silicone. In another embodiment, the projections may be formed from a semi-gas permeable material. The projections may be formed as an integral part of the sheets 402 and 403 and, therefore, they may also be formed from the same material as described above. In one embodiment, the projections may be solid, while in another embodiment the projections may be hollow to increase flexibility. The projections may form a plurality of channels and/or voids as described below to distribute reduced pressure and allow for fluid flow among the projections. The projections may be dimensioned to provide local load points at the tissue site 150 sufficient to create micro-strains at the tissue site 150 for stimulating granulation formation when reduced pressure is applied. The pattern and position of the projections may be uniform or non-uniform. The projections may have different shapes including, for example, the shape of a spike, cone, pyramid, dome, cylinder or rectangle. The shapes of the projections may be uniform or non-uniform depending on the tissue site 150. The shapes of the projections may occupy a volume defined by a cube volume where the side of the cube would range between approximately 0.2 mm to approximately 1.5 mm. In one embodiment, the spike shape may have a base width or diameter of about 0.2 mm and a vertical height of between about 0.4 mm and 0.8 mm. In another embodiment, the cone shape may have a base diameter of about 0.4 mm and a vertical height of between 0.4 mm to 1.2 mm. In yet another embodiment, the dome shape may have a spherical cap or parabolic shape with a base diameter ranging from about 0.4 mm to 1 mm.

In some other illustrative embodiments, the manifold 400 may further comprise chambers formed by interconnected closed cells to better distribute the apposition force applied to the manifold 400 as a result of the application of negative pressure because the volume of the chambers is greater than the volume of the individual closed cells. In one exemplary embodiment shown in FIG. 5, manifold 500 is similar in all respects to the manifold 400 comprising two sheets 502 and 503 of polymeric film having inner surfaces coupled to each other in a pattern defining a plurality of closed cells 504. The sheets 502 and 503 may be sealed to each other to form a sealed region 506 defining the closed cells 504. The sealed region 506 may also be perforated to provide pathways for fluid to flow through the manifold 500. In one exemplary embodiment, the sealed region 506 may comprise a plurality of apertures 505 that are formed between the closed cells 504 in the sealed region 506 that extend through both of the sheets 502 and 503 to permit fluid flow through the manifold 500. The manifold 500 also may comprise a plurality of passageways 508 fluidly coupling at least two of the closed cells 504 to form a closed chamber. In one exemplary embodiment, a closed chamber 548 is formed by all of the closed cells 504 in a row fluidly coupled by the passageways 508 as shown in FIG. 5. Closed chambers 548 may be formed in each of the other six rows as also shown in FIG. 5. The formation of closed chambers with closed cells in any pattern distributes apposition forces applied to the manifold 500 more equally across the manifold 500.

In one example embodiment, the manifold 500 may be manifold 510 that is similar in all respects to the manifold 500 and in many respects to the manifold 410 as shown in FIG. 5A1. More specifically, the manifold 510 comprises two sheets of polymeric film, sheet 512 and sheet 513, having inner surfaces coupled to each other in a pattern defining a plurality of closed cells 514. The sheets 512 and 513 may be sealed to each other in a sealed region 516 that defines the closed cells 514 that are generally hemispherical in shape. The manifold 510 also may comprise a plurality of passageways 518 interconnecting the closed cells 514 to form a closed chamber 558. The closed chamber 558 may be formed in only one of the sheets 512 and 513 so that they extend from only one side of the sealed region 516 as shown in FIG. 5A1.

In another example embodiment, the manifold 500 may be manifold 530 which is similar in all respects to the manifold 500 and in many respects to the manifold 430 as shown in FIG. 5A3. More specifically, the manifold 530 comprises two sheets of polymeric film, sheet 532 and sheet 533, having inner surfaces coupled to each other in a pattern defining a plurality of closed cells 534. The sheets 532 and 533 may be sealed to each other in a sealed region 536 that defines the closed cells 534 that are generally spherical in shape. The manifold 530 also may comprise a plurality of passageways 538 interconnecting the closed cells 534 to form a closed chamber 578. The closed chamber 578 is formed in both of the sheets 532 and 533 so that they extend from both sides of the sealed region 536 that provides more flexibility and cushioning then the closed chamber 558 extending from only one side of the sealed region 516.

In yet another example embodiment, the manifold 500 may be manifold 520 that is similar to the manifold 500 and in many respects to the manifold 420 as shown in FIG. 5A2. More specifically, the manifold 520 comprises two sheets of polymeric film, sheet 522 and sheet 523, having inner surfaces coupled or bonded to a third sheet 528 to form sealed region 526 defining a plurality of closed cells 524. The closed cells 524 are generally spherical in shape and formed by two hemispherical sections that are separated by portions of the third sheet 528. Sheet 522 and sheet 523 may be coupled or bonded to the third sheet 528 using a variety of different methods including, for example, melting (e.g., RF, ultrasonic, and heat), adhesives using both hot melt and solvents, and pressing techniques. The manifold 520 may also be formed by combining two of the manifolds 510 together by coupling or bonding the outside planar surface of the sheet 512 of each manifold 510 together to form the manifold 520. The third sheet 528 may be formed from a polymeric film and may also be perforated to permit airflow between the two hemispherical sections of the closed cells 524. When the third sheet 528 is formed from a polymeric material, the third sheet 528 may also be textured to provide wicking capability. The third sheet 528 may also be formed from a polyester material to provide wicking within the closed cells 524, and may further include fibers flocked into the polyester material to provide additional wicking capability. The third sheet 528 also may include an antimicrobial layer or antimicrobials coated on the third sheet 528.

Figure 6:
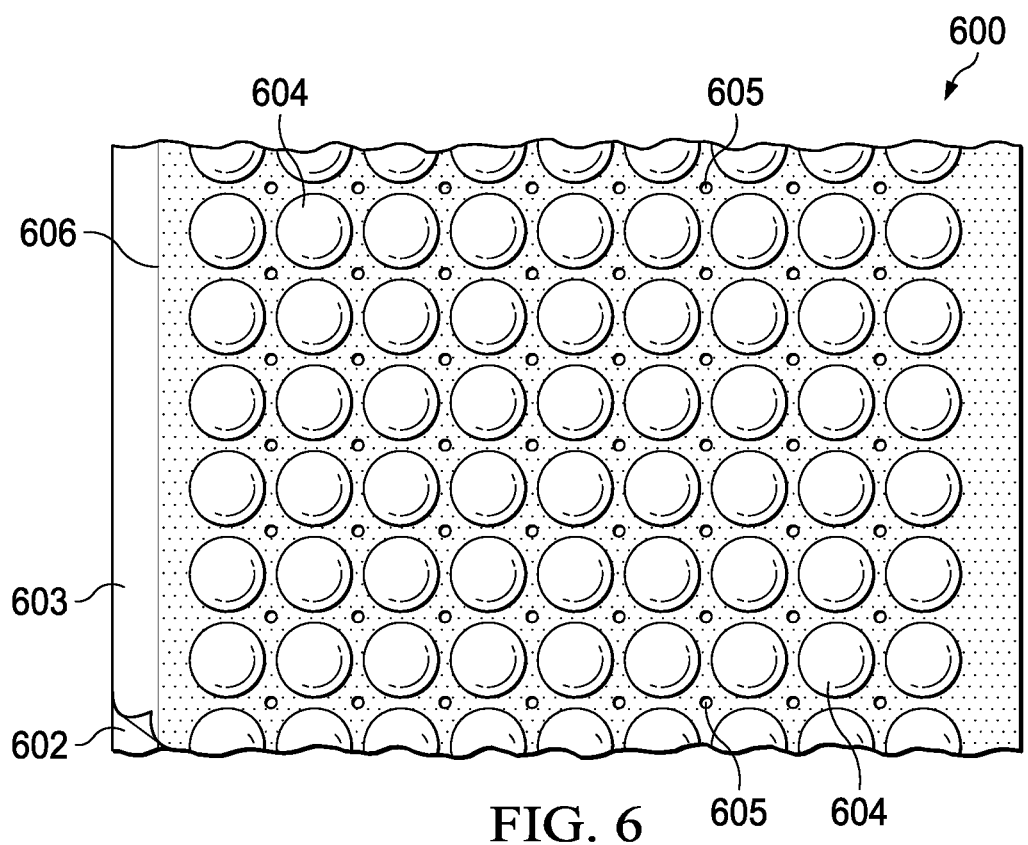
FIG. 6 is a plan view of a third embodiment of a sheet of closed cells formed from a web of nonporous, polymeric film that may be used as a manifold in the negative-pressure and instillation therapy system of FIGS. 1 and 1A.

The manifolds 400 and 500 both comprise two sheets 402, 403 and 502, 503 of polymeric film having inner surfaces sealed to each other in a pattern defining a plurality of closed cells 404 and 504 in close proximity to one another. The sheets 402, 403 and 502, 503 may be sealed to each other in a sealed region 406 and 506 that defines the closed cells 404. In both embodiments, the rows of the closed cells 404 and 504 are staggered so that the individual cells may be more closely nested together between the alternating rows to form a nested pattern of cells formed on the same plane as defined by the sealed regions 406, 506, respectively. In other embodiments, the closed cells may be arranged in other patterns suitable for the particular therapy being utilized. Referring to FIG. 6, for example, a manifold 600 also comprises two sheets 602 and 603 of polymeric film having inner surfaces sealed to each other in a pattern defining a plurality of closed cells 604 in close proximity to one another. However, the rows and columns of closed cells 604 are not staggered, but rather arranged in an aligned pattern. Depending on the diameter and pitch of the closed cells 604, the cell coverage percentage may range between about 10% and about 55% of the surface area of the manifold 600. The sheets 602 and 603 may be sealed to each other in a sealed region 606 that defines the closed cells 604. In this embodiment, the rows and columns of the closed cells 604 are arranged in line to form an aligned pattern. The manifold 600 may also include a sealed region 606 that may be perforated as described above. The pattern of closed cells may have a variety of different arrangements.

Figure 7:
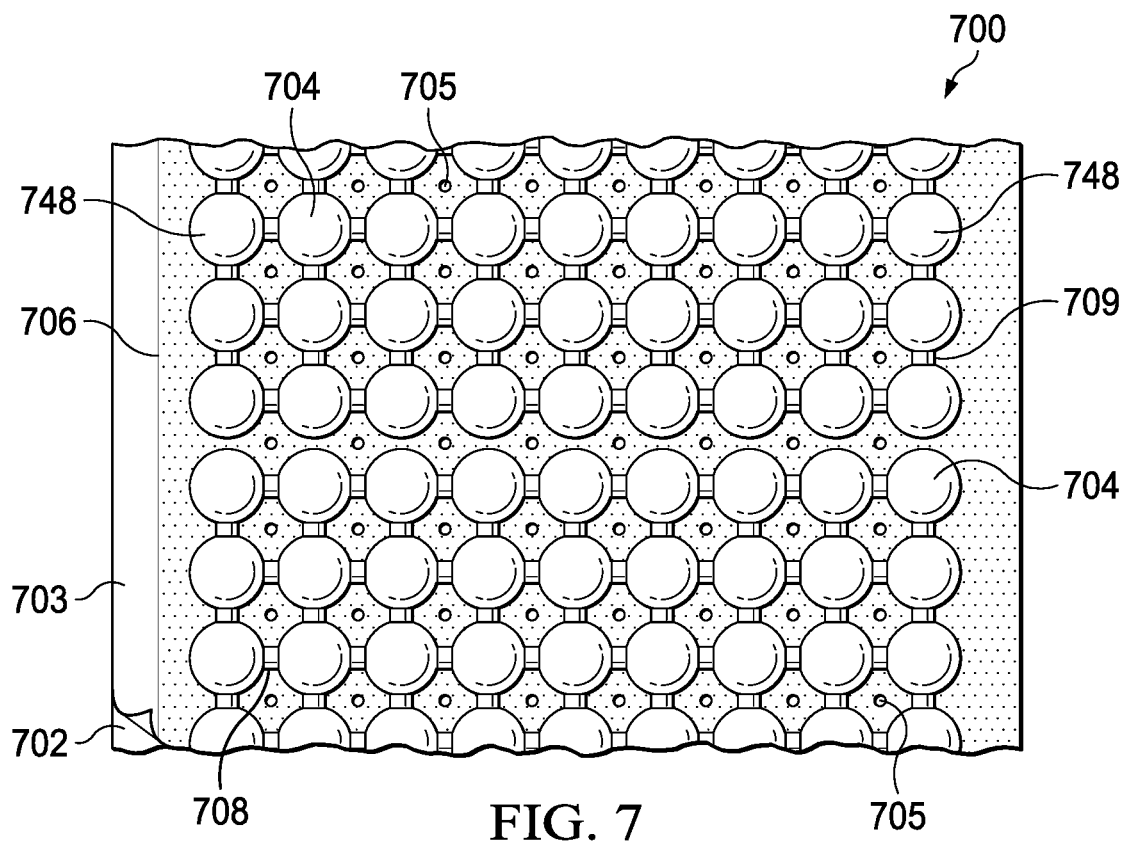
FIG. 7 is a plan view of a fourth embodiment of a sheet of closed cells formed from a web of nonporous, polymeric film that may be used as a manifold in the negative-pressure and instillation therapy system of FIGS. 1 and 1A.

In another exemplary embodiment shown in FIG. 7, manifold 700 is similar to the manifold 600 and comprises two sheets 702 and 703 of polymeric film having inner surfaces sealed to each other in a pattern defining a plurality of closed cells 704 in close proximity to one another. The sheets 702 and 703 may be sealed to each other in a sealed region 706 that defines the closed cells 704. The sealed region 706 may also be perforated to provide pathways for fluid to flow through the manifold 700. In one exemplary embodiment, the sealed region 706 may comprise a plurality of apertures 705 that are formed between the closed cells 704 in the sealed region 706 that extend through both of the sheets 702 and 703 to permit fluid flow through the manifold 700. The manifold 700 also may comprise a plurality of passageways 708 interconnecting the closed cells 704 to form a closed chamber. In one exemplary embodiment, a closed chamber 748 is formed by all of the closed cells 704 in a row fluidly coupled by the passageways 708 as shown in FIG. 7. Closed chambers 748 may be formed in each of the other six rows as also shown in FIG. 7. The formation of closed chambers 748 with closed cells 704 in any pattern may distribute apposition forces applied to the manifold 700 more equally across the manifold 700 as opposed to a manifold having only closed cells.

Figure 8:
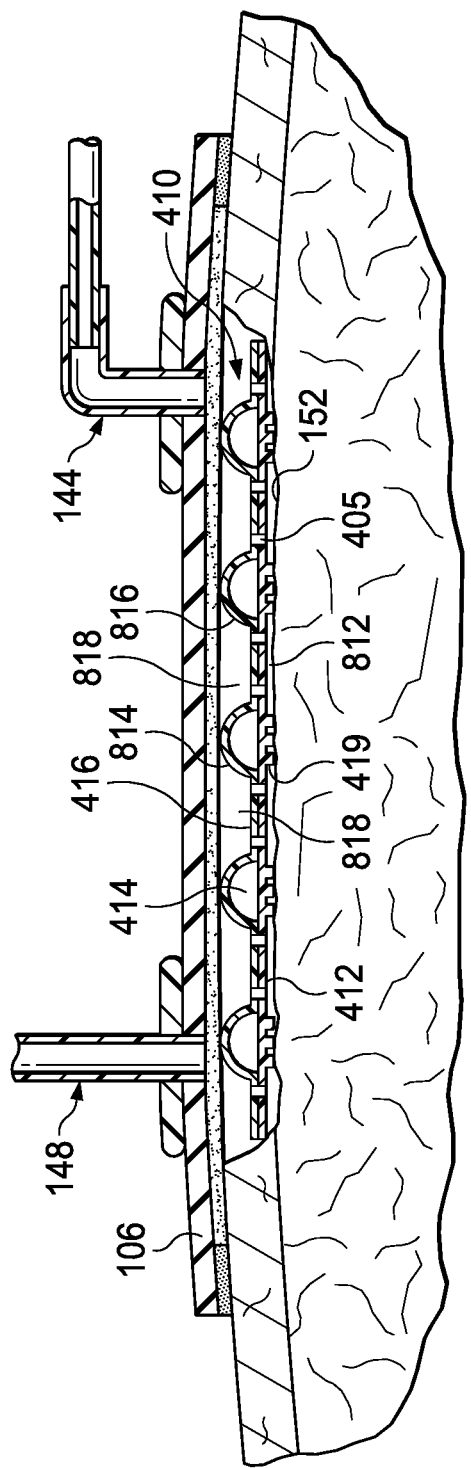
FIG. 8 is a schematic cross-section of the cover and manifold of the negative-pressure and instillation therapy system of FIGS. 1 and 1A for delivering negative pressure and treatment solutions, wherein the manifold is the manifold of FIG. 4A1.

Referring to FIG. 8, the dressing 102, which includes the cover 106 and the tissue interface 108, is shown wherein the tissue interface 108 is the manifold 140 and, more specifically, the manifold 410 shown in FIGS. 4A1 and 4B. In one embodiment, the manifold 410 may be disposed at the tissue site 150 so that the sheet 412 is positioned adjacent the wound 152 with the nodes 419 extending outwardly from the sheet 412 and contacting the wound 152. The nodes 419 may form voids 812 between the outside surface of the sheet 412 and the wound 152. The closed cells 414 have upper surfaces 814 that are adapted to contact the cover 106 when the cover 106 is placed over the manifold 410. The closed cells 414 also have side surfaces 816 that form a plurality of channels 818 with the cover 106 and the sealed region 416 for providing passageways for fluid flow for both negative pressure and instillation liquids during therapy sessions. The apertures 405 fluidly couple the channels 818 to the voids 812 so that the manifold 410 provides fluid communication from the fluid-delivery interface 148 to the tissue site 150 and from the tissue site 150 to the negative-pressure interface 144.

When negative pressure is applied to the manifold 410 in operation with or without the instillation of fluids as described above, the manifold 410 is compressed under the cover 106 during the decompression cycle creating an apposition force that causes the cover 106 to collapse toward the wound 152 because of the vacuum created within the voids 812 and the channels 818 via the apertures 405. The apposition force causes the cover 106 to collapse down on the upper surfaces of the closed cells 414 which is transmitted via the closed cells 414 to the nodes 419 to increase micro-strains on the wound 152 to enhance granulation. Although the closed cells 414 may change shape or flatten somewhat during the application of negative pressure to the manifold 410, the volume of the closed cells 414 remains substantially constant as described above so that the manifold 410 transmits apposition forces to the nodes 419 while maintaining fluid flow through the channels 818 to continue providing negative pressure therapy to the wound 152. Consequently, the manifold 410 applies apposition forces to the nodes 419 which enhance granulation while maintaining fluid communication with the tissue site 150 via the channels 818 and the voids 812. The flexibility of the closed cells 414 also facilitates movement of the nodes 419 as the negative pressure increases during the decompression cycle and/or is varied during treatment so that the additional movement further enhances granulation.

Figure 9:
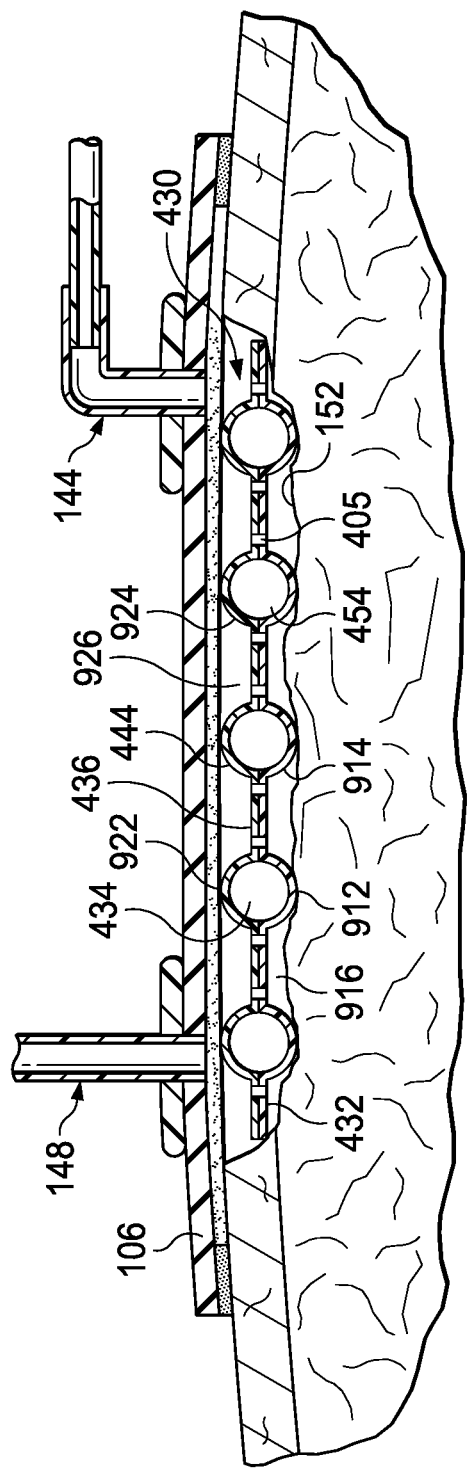
FIG. 9 is a schematic cross-section of the cover and manifold of the negative-pressure and instillation therapy system of FIGS. 1 and 1A for delivering negative pressure and treatment solutions, wherein the manifold is the manifold of FIG. 4A3.

Referring to FIG. 9, the dressing 102, which includes the cover 106 and the tissue interface 108, is shown wherein the tissue interface 108 is the manifold 140 and, more specifically, the manifold 430 shown in FIG. 4A3. In one embodiment, the manifold 430 may be disposed at the tissue site 150 so that the sheet 432 is positioned facing the wound 152 with the hemispherical cells 454 extending outwardly from the sheet 432 toward the wound 152. The hemispherical cells 454 have proximal surfaces 912 that are adapted to contact the wound 152 when the manifold 430 is disposed at the tissue site 150. The closed cells 434 also have side surfaces 914 that form a plurality of proximal channels 916 with the wound 152 and the sealed region 436 for providing passageways for fluid flow for both negative pressure and instillation liquids during therapy sessions for the wound 152. The hemispherical cell 444 portions of the closed cells 434 have distal surfaces 922 that are adapted to contact the cover 106 when the cover 106 is placed over the manifold 430. The hemispherical cell 444 portions of the closed cells 434 also have side surfaces 924 that form a plurality of distal channels 926 with the cover 106 and the sealed region 436 for providing passageways for fluid flow for both negative pressure and instillation liquids during therapy sessions. The apertures 405 fluidly couple the proximal channels 916 and the distal channels 926 so that the manifold 430 provides fluid communication from the fluid-delivery interface 148 to the tissue site 150 and from the tissue site 150 to the negative-pressure interface 144.

When negative pressure is applied to the manifold 430 in operation with or without the instillation of fluids as described above, the manifold 430 is compressed under the cover 106 during the compression cycle creating an apposition force that causes the cover 106 to collapse toward the wound 152 because of the vacuum created within the proximal channels 916 and the distal channels 926 via the apertures 405. The apposition force causes the cover 106 to collapse down on the distal surfaces 922 of the closed cells 434 which is transmitted via the closed cells 434 to the proximal surfaces 912 of the hemispherical cells 454 to increase micro-strains on the wound 152 for enhancing granulation. Although the closed cells 434 may flatten somewhat during the application of negative pressure to the manifold 430, the volume the closed cells 434 remains substantially constant so that the manifold 430 transmits the apposition force is to the proximal surfaces 912 of the hemispherical cells 454 while maintaining fluid flow through the proximal channels 916 and the distal channels 926 to continue providing negative pressure therapy to the wound 152. Consequently, the manifold 430 applies apposition forces to the proximal surfaces 912 and/or the nodes 429 (not shown in FIG. 9) which enhance granulation while maintaining fluid communication with the tissue site 150 via the proximal channels 916 and the distal channels 926. The flexibility of the closed cells 434 also facilitates movement of the proximal surfaces 912 of the hemispherical portion 454 as the negative pressure increases during the decompression cycle and/or is varied during treatment so that the additional movement further enhances granulation.

The manifold 410 and manifold 430 are a single component comprising closed cells 414 and 434, respectively, separated by sealed regions 416 and 436, respectively, and apertures 405 extending through the sealed regions such that the manifolds provide both a manifold function and a filler function. The manifold function provides fluid flow for both negative pressure and instillation liquids, while the filler function provides spacing between the tissue site 150 and the cover 106 with material having sufficient flexibility and tensile strength to prevent the manifold from collapsing in order to maintain fluid flow. The apposition force causes the cover 106 to collapse down on the manifold which is transmitted via the closed cells to increase micro-strains on the wound 152 thereby enhancing granulation.

Moreover, the method of dressing a wound is simpler and quicker because a caregiver places only one component in contact with the tissue site rather than two separate components, i.e., a separate manifold member and a separate filler member. When the method of dressing a wound requires two separate members, a caregiver must first size and place a manifold member in contact with the tissue site and then position the filler member above the manifold member which requires more time and is more difficult. Often the filler member must be adjusted to substantially fill the space beneath the cover and be trimmed and resized to properly interface with the manifold member. Using the single-component manifolds described herein is less complicated and requires less time for dressing a wound than previous methods requiring the use of two members which can reduce the possibility of infection and other challenges inherent in previous methods of dressing wounds. Additionally, the single-component manifolds also provide better fluid flow because the fluids are not impeded by a separate filler member that might not be sufficiently porous or perforated to accommodate instillation fluids or negative pressure during the treatment process as described above.

All of the manifolds described above may also comprise tear paths formed in the polymeric film that allow a caregiver to tear the manifold into separate components to properly size a manifold for positioning in contact with the tissue site. The tear paths may define multiple regions of the film wherein the smallest region has an area greater than 20 cm$^2$. The tear paths may be non-leaking so that the composite manifold may still be utilized when not torn into separate components. In one example embodiment, the tear paths may be formed by indentations in the polymeric film that provide a weakened path in the film to facilitate tearing by a caregiver. In another example embodiment, the film may comprise two sheets of polymeric film wherein the non-leaking tear paths are formed by perforations in at least one of the two sheets of polymeric film. If perforations are formed in both of the two sheets of polymeric film to further facilitate tearing, the perforations in one of the two sheets may be aligned but out of registration with the perforations in the other one of the two sheets so that the tear paths do not leak. Using a manifold that comprises tear paths may simplify the method of dressing a wound as described above because it is easier and quicker to size the manifold when treating the tissue site.

Referring to FIGS. 10A and 10B, both are charts that illustrate the negative pressure variations (mmHg) over time (minutes) for pressure measurements at the container 112 as compared to the pressure measurements at different locations around the wound. For a wound generally rectangular in shape, the pressure was measured at the (i) bottom of the wound 152, (ii) one of the edges of the short or width side of the wound, and (iii) one of the edges of the long or length side of the wound. The negative pressure initially is cycled on and off for approximately every two minutes after instillation of 60 mL of a saline solution, and then held at a target pressure of approximately 120 mmHg More specifically, FIGS. 10A and 10B illustrate these measurements for a manifold such as, for example, the manifold 430 having closed cells 434 with an average diameter of about 1 mm, wherein the manifold measured in FIG. 10A had no apertures 405 while the manifold tested in FIG. 10B included apertures 405. When utilizing the manifold 430 without any apertures 405, the pressures measured at both the short side edge and the long side edge of the wound 152 drops as low as 60 mmHg for a period of time while the manifold 430 that includes apertures 405 is measured fairly steadily at 120 mmHg except for a brief period of time where the pressure drops to about 100 mmHg. The pressure measurements at the bottom of the wound 152 are even more dramatic. When utilizing the manifold 430 without any apertures 405, the pressure measured at the bottom of the wound 152 is only 20 mmHg and stays there, whereas the pressure at the bottom of the wound 152 when utilizing the apertures 405 is measured fairly steadily at 100 mmHg Thus, it is desirable that the example embodiments of the manifolds described above, i.e., the manifolds 400, 500, 600 and 700, include apertures as described above including, for example, apertures 405, 505, 605 and 705.

In another example embodiment, the manifold 140 may comprise at least two layers of manifolds, e.g., the manifolds 400, 500, 600 and 700, wherein the two layers include symmetric closed cells such as, for example, hemispherical closed cells that face each other in a complementary orientation. Referring back to FIG. 8, the manifold 140 may include two of the manifolds 410 wherein the hemispherical surface of the closed cells 414 of each of the two manifolds 410 face each other such that the sheet 412 of the manifold 410 adjacent the cover 106 (not shown), i.e., the upper manifold, contacts the cover 106. In one embodiment, the closed cells 414 of the two manifolds 410 may be nested together so that the upper surfaces 814 of each one face the sealed region 416 of the other. In other words, the closed cells 414 of the two manifolds 410 may be nested together such that the sealed regions 416 of the two manifolds 410 are located in separate planes. In order that the manifold 140 including the two manifolds 410 fit within the tissue site 150 under the cover 106, diameter and pitch of the hemispherical surface of the closed cells 414 may be varied to fit within the tissue site 150 and to accommodate different type of wounds and therapies being provided. As indicated above, the closed cells 414 may have a diameter between about 0.5 mm and 10 mm and a pitch between about 1.5 mm and 15 mm depending on the depth of the wound 152 at the tissue site 150. The manifold 140 including the two manifolds 410 may increase the apposition force being applied to the wound 152 to further enhance granulation.

Figure 11:
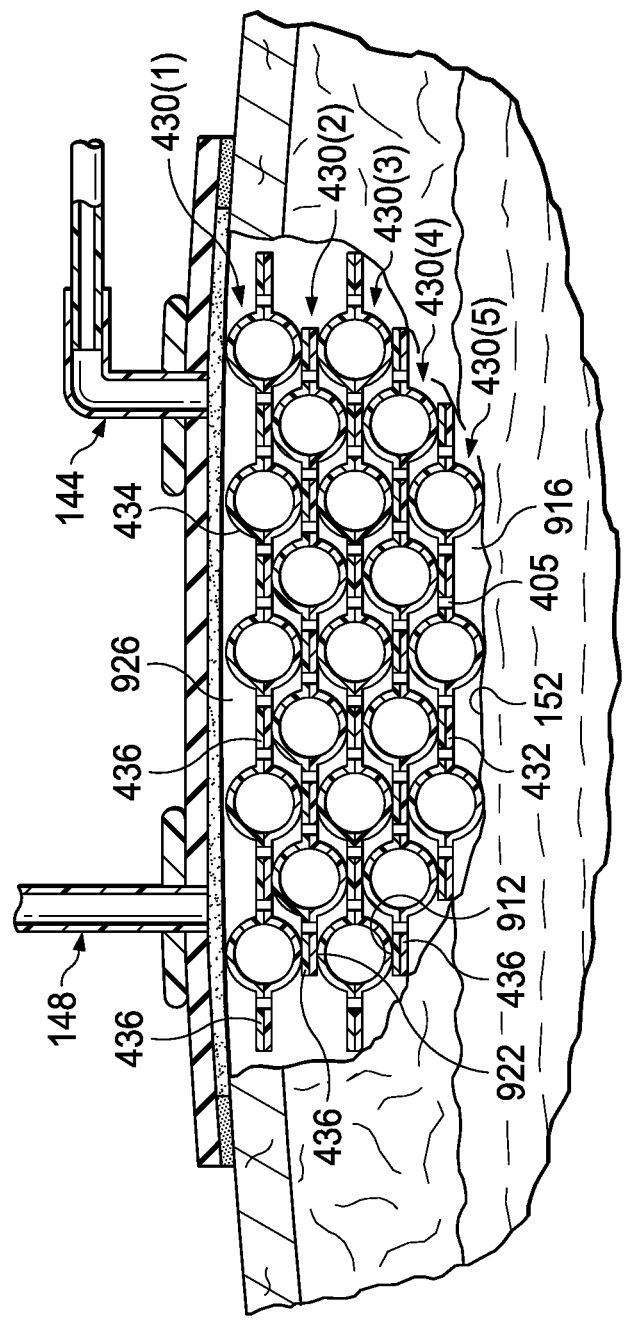
FIG. 11 is a schematic cross-section of the cover and manifold of the negative-pressure and instillation therapy system of FIGS. 1 and 1A for delivering negative pressure and treatment solutions, wherein the manifold is a multilayer structure comprising five layers of the manifold of FIG. 4A3.

In yet another example embodiment, the manifold 140 may comprise more than one layer of manifolds, e.g., the manifolds 400, 500, 600 and 700, wherein the multiple layers include more symmetrical closed cells such as, for example, spherical closed cells that may be stacked one on top of the other to form a single manifold. Referring to FIGS. 9 and 11, the manifold 140 may include, for example, five manifolds 430, i.e., stacked manifolds 430(1)-430(5), stacked one on top of the other to form the manifold 140 that may be used for a deeper wound 152 as shown in FIG. 11 or a subcutaneous wound (not shown). In this particular embodiment, the closed cells 434 also may be nested together so that the proximal surfaces 912 and the distal surfaces 922 of each one face the sealed region 436 of the other as shown for the stacked manifold 430(3) to form a block of closed cells 434 as the manifold 140. In other words, the closed cells 434 of the stacked manifolds 430(1)-430(5) may be nested together such that the sealed regions 436 of the manifolds are located in separate planes. The proximal channels 916 and distal channels 926 are also formed as described above including those disposed between each of the stacked manifolds 430(1)-430(5). As indicated above, a multilayer manifold may be necessary for deeper wounds 152 that may require greater apposition forces to further enhance granulation for more rapidly healing the wound 152.

Figure 12:
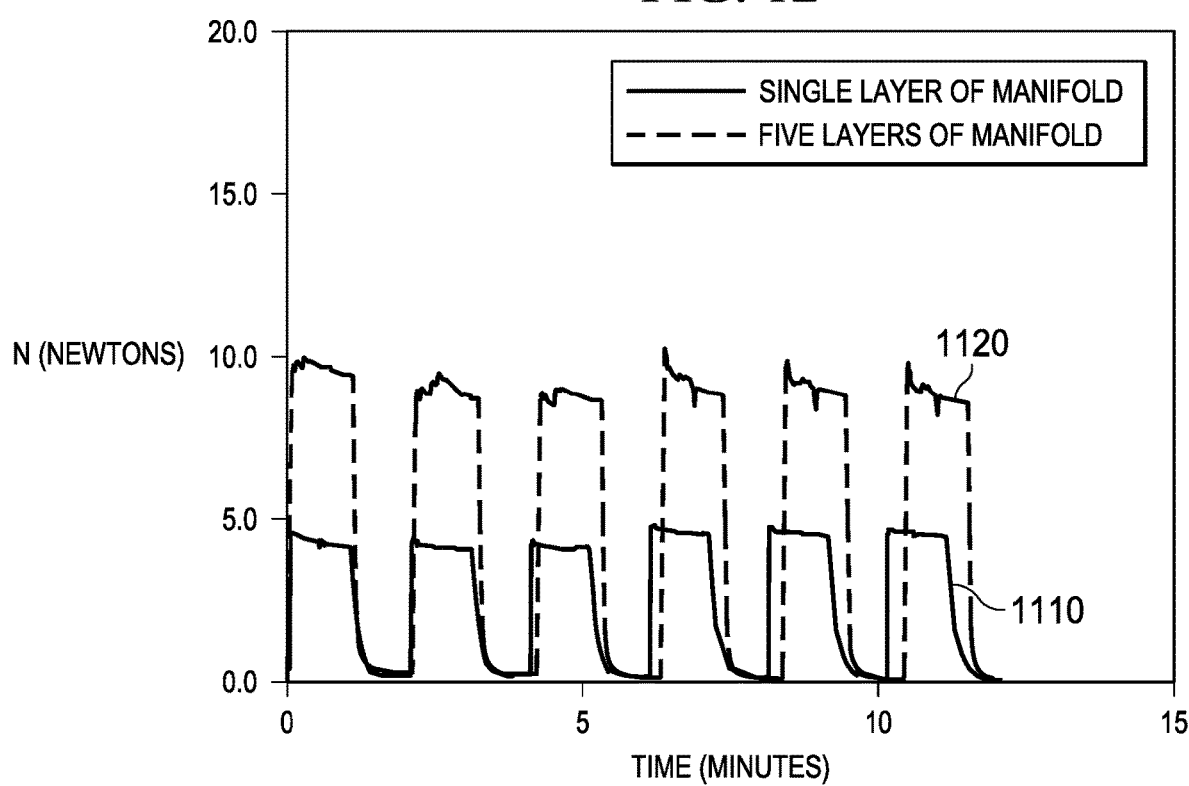
FIG. 12 is a chart illustrating two graphs of the load in newtons (N), i.e., the apposition force, being applied to a tissue site by negative pressure via the manifolds of FIGS. 9 and 11 with the negative pressure cycling on and off intermittently, one minute on and one minute off, including three cycles each of 125 mmHg and 200 mmHg during the on cycles.

Referring to FIG. 12, a chart is shown that illustrates two graphs, graph 1110 and graph 1120, of the load in newtons (N), i.e., the apposition force, being applied to a tissue site by negative pressure over time with the negative pressure cycling intermittently on and off, one minute on and one minute off, including three cycles each of 125 mmHg and 200 mmHg during the on cycles. The graph 1110 is the apposition force resulting from the application of negative pressure to the manifold 140 comprising a single layer that is the manifold 430 shown in FIG. 9. The apposition force for this single layer manifold varied between approximately 4.0 and 4.5 N when the negative pressure being applied was approximately 125 mmHg and varied between approximately 4.5 and 4.7 N when the negative pressure being applied was approximately 200 mmHg. The graph 1120 is the apposition force resulting from the application of negative pressure to the manifold 140 comprising a multilayer structure comprising five layers of the manifold 430 as shown in FIG. 10. The apposition force for this multilayer manifold varied between approximately 9 and 10 N when the negative pressure being applied was approximately 125 mmHg and varied between approximately 9 and 11 N when the negative pressure being applied was approximately 200 mmHg. As can be seen, the apposition force more than doubles when utilizing a multilayer manifold structure that further enhances granulation without sacrificing fluid communication of instillation fluids and negative pressure through the manifold structure as a result of the proximal channels 916 and the distal channels 926 formed among the closed cells 434.

Without limiting the mechanism, function or utility of present technology, the systems and methods described herein may provide significant advantages relative to treatment modalities among those known in the art. For example, the manifolds 400, 500, 600 and 700 may have nodes or textures that are embossed or welded on the manifold so that no material may be left at the tissue site when removed. Moreover, because the manifolds 400, 500, 600 and 700 are formed from polymeric material with integrated nodes or textures, the amount of tissue ingrowth by the manifolds may be minimized or eliminated which ameliorates the pain or discomfort when the manifolds are removed from the tissue site after the negative pressure and instillation therapies have been applied. Consequently, such manifolds may be left at the tissue site for longer periods of time before they need to be replaced, but still generate more macro and micro strains at the tissue site to enhance granulation without significant tissue ingrowth or shedding remnants of material when removed.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for treating a tissue site, comprising:
   a manifold including a non-porous film having a plurality of closed cells containing fluid, passageways fluidly coupling at least two of the closed cells together to form a closed chamber, apertures disposed in the film between the closed cells and extending through the film to allow fluid flow between a first side and a second side of the manifold, and surface features on at least an outer surface of at least some of the closed cells;
   a cover adapted to provide a fluid seal between a therapeutic environment including the tissue site and the manifold on one side of the cover and a local external environment on the other side of the cover; and
a negative-pressure source fluidly coupled to the therapeutic environment and adapted to provide negative pressure through distal channels formed between the manifold and the cover and the apertures to the tissue site.

2. The system of claim 1, wherein the film further comprises at least one non-leaking tear path configured to facilitate tearing the manifold into separate components.

3. The system of claim 2, wherein the film further comprises two sheets of polymeric film, and wherein the at least one non-leaking tear path is formed by perforations in at least one of the two sheets of polymeric film.

4. The system of claim 1, wherein the film further comprises non-leaking tear paths defining multiple regions of the film wherein the smallest region has an area greater than 20 cm².

5. The system of claim 1, wherein the surface features include ridges and grooves.

6. The system of claim 1, wherein the surface features are embossed on film.

7. The system of claim 1, wherein the surface features have a depth or height in the range of about 0.4 mm to about 1.5 mm.

8. The system of claim 1, wherein the non-porous film comprises two sheets of polymeric film having inner surfaces sealed to each other to form a sealed region.

9. The system of claim 8, wherein the plurality of closed cells are formed in a first one of the two sheets of polymeric film.

10. The system of claim 9, wherein the closed cells have a volumetric shape that is any one of a hemispherical, conical, cylindrical, or geodesic shape.

11. The system of claim 9, further comprising nodes projecting outwardly from a second one of the two sheets of polymeric film and adapted to form proximal channels between the seals and the tissue site in fluid communication with the apertures.

12. The system of claim 9, further comprising a grid projecting outwardly from a second one of the two sheets of polymeric film and adapted to form proximal channels between the seals and the tissue site in fluid communication with the apertures.

13. The system of claim 8, wherein the plurality of closed cells are formed in both of the two sheets of polymeric film.

14. The system of claim 13, wherein the closed cells have a volumetric shape that is any one of a hemispherical, conical, cylindrical, or geodesic shape.

15. The system of claim 13, wherein the closed cells have a volumetric shape that is generally hemispherical and coincide with each other on both sheets to form a generally spherical shape.

16. The system of claim 13, wherein distal channels are formed between the closed cells of a first one of the two sheets of polymeric film and wherein proximal channels are formed between the closed cells of a second one of the two sheets of polymeric film in fluid communication with the distal channels through the apertures.

17. The system of claim 16, further comprising nodes projecting outwardly from the closed cells of the second one of the two sheets of polymeric film adjacent the proximal channels.

18. The system of claim 13, further comprising a grid projecting outwardly from the closed cells of the second one of the two sheets of polymeric film adjacent the proximal channels.

19. The system of claim 1, wherein the non-porous film comprises three sheets of polymeric film including two outer sheets and one internal sheet having surfaces sealed to each other to form a sealed region.

20. The system of claim 19, wherein the plurality of closed cells are formed in one of the two outer sheets of polymeric film.

21. The system of claim 19, wherein the plurality of closed cells are formed in both of the two outer sheets of polymeric film.

22. The system of claim 21, wherein the closed cells have a volumetric shape that is generally hemispherical and coincide with each other on the two outer sheets to form a generally spherical shape divided by the inner sheet.

23. The system of claim 1, further comprising a processor operatively coupled to the negative-pressure source to provide a target pressure to the therapeutic environment in a pressure control mode.

24. The system of claim 23, wherein the pressure control mode is a continuous pressure mode.

25. The system of claim 23, wherein the pressure control mode is an intermittent pressure mode.

26. The system of claim 1, further comprising a processor operatively coupled to the negative-pressure source to provide a variable target pressure to the therapeutic environment in a dynamic pressure mode.

27. The system of claim 1, further comprising a positive-pressure source fluidly coupled to the therapeutic environment and adapted to deliver a solution through the apertures to the tissue site.

28. The system of claim 27, further comprising a processor operatively coupled to the positive-pressure source to provide the solution to the therapeutic environment in a predetermined dosage.

29. The system of claim 27, further comprising a processor operatively coupled to the positive-pressure source to provide the solution to the therapeutic environment for a predetermined time.

30. The system of claim 27, further comprising a processor operatively coupled to the positive-pressure source to provide the solution to the therapeutic environment at a predetermined rate over time.

31. The system of claim 27, further comprising a processor operatively coupled to the negative-pressure source and the positive-pressure source to provide negative pressure to the therapeutic environment prior to providing the solution to the therapeutic environment.

32. The system of claim 27, further comprising a processor operatively coupled to the negative-pressure source and the positive-pressure source to provide negative pressure to the therapeutic environment while providing the solution to the therapeutic environment.

33. The system of claim 1, wherein the plurality of closed cells are generally hemispherical and have a diameter between about 0.5 mm and 10 mm.

34. The system of claim 1, wherein the plurality of closed cells are generally hemispherical and have a pitch between about 1.5 mm and 15 mm.

35. The system of claim 1, wherein the non-porous film comprises two sheets of polymeric film having inner surfaces sealed to each other to form a sealed region having a thickness between about 10 µm and 1000 µm.

36. The system of claim 1, wherein the closed cells are formed in a pattern of rows and columns.

37. The system of claim 36, further comprising passageways fluidly coupling the closed cells in at least one of the rows to form a closed chamber.

38. The system of claim 36, wherein the rows are formed in a nested pattern.

39. The system of claim 36, wherein the rows are formed in an in-line pattern.

40. The system of claim 36, wherein the closed cells have a generally spherical shape.

41. The system of claim 1, wherein the closed cells have a generally spherical shape.

42. The system of claim 1, wherein the closed cells have a geodesic shape.

43. A method for treating a tissue site, comprising:
   positioning a manifold including a non-porous film having a plurality of closed cells and apertures extending through the film, at least two of the closed cells being fluidly coupled by passageways to form a closed chamber, the closed cells and apertures defining fluid flow paths;
   covering the manifold and the tissue site with a drape to provide a fluid seal between a therapeutic environment including the manifold on one side of the drape and a local external environment the other side of the drape; and
   providing negative pressure from a negative-pressure source coupled to the therapeutic environment wherein the negative pressure is applied to the tissue site through the fluid flow paths.

44. The method of claim 43 wherein the positioning step includes placing the manifold on a surface wound.

45. The method of claim 43, further comprising delivering a solution from a solution source fluidly coupled to the therapeutic environment wherein the solution is applied through the apertures to the tissue site.

46. The method of claim 43, further providing a target pressure from the negative-pressure source to the therapeutic environment in a pressure control mode.

47. The method of claim 46, wherein the pressure control mode is a continuous pressure mode.

48. The method of claim 46, wherein the pressure control mode is an intermittent pressure mode.

49. The method of claim 43, further providing a variable target pressure from the negative-pressure source to the therapeutic environment in a dynamic pressure mode.

* * * * *